(12) United States Patent
Pollitt et al.

(10) Patent No.: US 6,887,848 B2
(45) Date of Patent: May 3, 2005

(54) VASCULAR ENDOTHELIAL GROWTH FACTOR VARIANTS

(75) Inventors: N. Stephen Pollitt, Los Altos, CA (US); Judith A. Abraham, San Jose, CA (US)

(73) Assignee: Scios, Inc., Fremont, CA (US)

( * ) Notice: Subject to any disclaimer, the term of this patent is extended or adjusted under 35 U.S.C. 154(b) by 0 days.

(21) Appl. No.: 10/268,447

(22) Filed: Oct. 10, 2002

(65) Prior Publication Data

US 2003/0096754 A1 May 22, 2003

Related U.S. Application Data

(62) Division of application No. 09/574,708, filed on May 18, 2000, now Pat. No. 6,475,796.
(60) Provisional application No. 60/135,312, filed on May 20, 1999.

(51) Int. Cl.⁷ ........................ A61K 38/00; C07K 14/00; C12N 15/63
(52) U.S. Cl. ........................ 514/2; 530/350; 435/455
(58) Field of Search ............................ 514/2; 530/350; 435/455

(56) References Cited

U.S. PATENT DOCUMENTS

| | | | |
|---|---|---|---|
| 3,187,748 A | 6/1965 | Mitchell et al. | |
| 3,565,070 A | 2/1971 | Hanson et al. | |
| 3,658,059 A | 4/1972 | Steil | |
| 3,814,297 A | 6/1974 | Warren | |
| 3,826,413 A | 7/1974 | Warren | |
| 4,527,769 A | 7/1985 | Stogner et al. | |
| 4,592,348 A | 6/1986 | Waters, IV et al. | |
| 4,648,393 A | 3/1987 | Landis et al. | |
| 4,677,975 A | 7/1987 | Edgar et al. | |
| 4,790,305 A | 12/1988 | Zoltan et al. | |
| 4,803,978 A | 2/1989 | Johnson, IV et al. | |
| 4,812,405 A | 3/1989 | Lair et al. | |
| 4,818,700 A | 4/1989 | Cregg et al. | |
| 4,896,832 A | 1/1990 | Howlett | |
| 4,926,852 A | 5/1990 | Zoltan et al. | |
| 4,943,529 A | 7/1990 | Van Den Berg et al. | |
| 4,952,496 A | 8/1990 | Studier et al. | |
| 4,992,901 A | 2/1991 | Keel et al. | |
| 5,194,596 A | 3/1993 | Tischer et al. | |
| 5,219,739 A | 6/1993 | Tischer et al. | |
| 5,240,848 A | 8/1993 | Keck et al. | |
| 5,244,460 A | 9/1993 | Unger et al. | |
| 5,332,671 A | 7/1994 | Ferrara et al. | |
| 5,378,613 A | 1/1995 | Belagaje ..................... 435/69.7 |
| 5,595,888 A | 1/1997 | Gray et al. .............. 435/69.51 |
| 5,648,233 A | 7/1997 | Yamaguchi et al. ....... 435/69.1 |
| 5,665,600 A | 9/1997 | Hagenson et al. | |
| 5,693,489 A | 12/1997 | Studier et al. | |
| 5,705,362 A | 1/1998 | Bonekamp et al. ......... 435/69.8 |
| 5,783,416 A | 7/1998 | Thim et al. ................ 435/69.1 |
| 5,785,965 A | 7/1998 | Pratt et al. ................ 424/93.21 |
| 5,935,820 A | 8/1999 | Hu et al. .................... 435/69.4 |
| 6,013,780 A | 1/2000 | Neufeld et al. ............. 536/23.1 |
| 6,475,796 B1 | 11/2002 | Pollitt et al. ................ 435/455 |

FOREIGN PATENT DOCUMENTS

| | | |
|---|---|---|
| EP | 0370989 | 11/1989 |
| EP | 0484401 | 7/1990 |
| WO | B0484401 | 2/1991 |
| WO | WO 93/12142 | 6/1993 |
| WO | WO 96/06641 | 3/1996 |
| WO | WO 97 08313 | 3/1997 |
| WO | WO98/10071 | 3/1998 |
| WO | WO 98/16551 | 4/1998 |
| WO | WO98/2411 | 6/1998 |
| WO | WO 98/24811 | 6/1998 |

OTHER PUBLICATIONS

Khan et al. Exp. Opin. Pharmacother. 2003, vol. 4(2), pp. 219–226.*
Belagaje et al. (1997). *Protein Sci* 6(9):1953–62.
Ben–Bassatt (1991). *Bioprocess Tech* 12:147–159.
Breier et al. (1992). *Development* 114:521–532.
Christinger et al. (1996). *Proteins: Structure, Function, & Genetics* 26:353–357.
Claffey et al. 1995). *Biochimica et Biophysica Acta* 1246:1–9.
Dalboge et al. (1987) *Bio/Tech* 5:161–164.
Ferrara et al. (1991). *J Cell Biochem* 47(3):211–218.
Patel et al. (1999). *Human Gene Therapy* 10(8).
Poetgens et al. (1994). *J Bio Chem* 269(52):32879–32885.
International Search Report mailed on Oct 18, 2000 for PCT patent application No. PCT/US00/13536 filed on May 18, 2000, 4 pages.
Achen et al. "Vascular endothelial growth factor D (VEGF–D) is a ligand for the tyrosine kinases VEGF receptor 2(Flk1) and VEGF receptor 3(Flt4)" *Proc. Natl. Aca. Sci.* 95:548–553 (1998).
Altschul et al., "Gapped BLAST and PSI–BLAST: a new generation of protein database programs", *Nucleic Acids Res.*, 25:3389–3402 (1997).
Ausubel et al., "Current Protocols in Molecular Biology" eds. (1987).
Beach and Nurse, "High–frequency transformation of the fission yeast *Schizosaccharomyces pombe*" *Nature* 290:140 (1981).

(Continued)

Primary Examiner—Janet Andres
(74) Attorney, Agent, or Firm—Morrison & Foerster LLP

(57) ABSTRACT

The invention is directed to a method of enhancing the biological activity of vascular endothelial growth factors (VEGF). The invention further concerns certain VEGF variants having enhanced biological activity, methods and means for preparing these variants, and pharmaceutical compositions comprising them. In a further aspect, the invention concerns methods of treatment using, and articles of manufacture containing such VEGF variants.

17 Claims, 17 Drawing Sheets

OTHER PUBLICATIONS

C. Anthony, "The Biochemistry of Metholotrophis" *Department of Biochemistry University of Southampton,* England, 269 (1982).

Cohen et al., "High levels of Biologically Active Vascular Endothelial Growth Factor (VEGF) are Produced by the Baculovirus Expression System", *Growth Factors* 7:131–138 (1993).

Cohen et al., "VEGF121, a Vascular Endothelial Growth Factor (VEGF) Isoform Lacking Heparin Biding Ability, Requires Cell–Surface Heparin Sulfates for Efficient Binding to VEGF Receptors of Human Melanoma Cells", *J. Biol. Chem.* 270:11322–11326 (1995).

Conn et al., "Purification of glycoprotein vascular endothelial cell mitogen from a rat glioma–derived cell line", *PNAS USA*, 87:1323–1327 (1990)

Connolly et al., "Human Vascular Permeability Factor" *J. Biol Chem.* 264:20017–20024 (1989).

Connolly et al., "Tumor Vascular Permeability Factor Stimulates Endothelial Cell Growth and Angiogenesis", *J. Clin. Invest.* 84: 1470–1478 (1989).

Cregg et al., "High–Level Expression and Efficient Assembly of Hepatitis B Surface Antigen in: The Methylotrophic Yeast, Pichia Pastoris", *Bio/Technology 5:* 479–485 (1987).

Dvorak et al. "Distribution of Vascular Permeability Factor (Vascular Endothelial Growth Factor) in Tumors: Concentration in Tumor Blood Vessels", *J. Exp. Med.* 174:1275–1278 (1991).

Ferrara and Henzel, "Pituitary Follicular Cells Secrete a Novel Heparin–Binding Growth Factor Specific For Vascular Endothelial Cells", *Biochem. Biophys. Res. Comm.* 161:851–858 (1988).

Fiebich et al., "Synthesis and assembly of functionally active human vascular endothelial growth factor homodimers in insect cells", *Eur. J. Biochem* 211:19–26 (1993).

Fiers et al., "Complete nucleotide sequence of SV50DNA", *Nature 273:*113 (1978).

Freshney, "Animal Cell Culture", ed. IRL Press (1987).

Gait, "Oligonucleotide Synthesis" ed. IRL Press (1984).

Gitay–Goren et al., "Selective Binding of VEGF121 to One of the Three Vascular Endothelial Growth Factor Receptors of Vascular Endothelial Cells", *J. Biol. Chem.* 271:5519–5523 (1996).

Goeddel et al., "Direct expression in *Escherichia coli* of a DNA sequence coding for human growth hormone", *Nature 281:*544 (1979).

Gospodarowicz et al., "Isolation and Characterization of a Vascular Endothelial Cell Mitogen produced by Pituitary-Derived Folliculo Stellate Cells", *PNAS USA,* 86:7311–7315 (1989).

Goto et al., "Synergistic Effects of Vascular Endothelial Growth Factor and Basic Fibroblast Growth factor on the Proliferation and Cord Formation of Bovine Capillary Endothelial Cells within Collagen Gels", *Lab. Invest. 69:*508–517 (1993).

Graham et al, "Characteristics of Human Cell Line Transformed by DNA from Human Adenovirus Type 5", *J. Gen. Virol. 36:*59 (1977).

Hinnen, et al., "Transformation of yeast", *Proc. Natl. Acad. Sci. USA* 75:1929–1933 (1978).

Hitzeman et al., "Isolation and Characterization of the Yeast 3–Phosphoglycerokinase Gene (PGK) by an immunological Screening Technique", *J. Biol. Chem. 255:*2073 (1980).

Holland et al., "Isolation and Identification of Yeast Messenger Ribonucleic Acids Coding for Enolase, Glyceraldehyde–3–Phosphate Dehydrogenase, and Phosphoglycerate Kinase", *Biochemistry,* 17:4900 (1978).

Houck et al., Dual regulation of vascular endothelial growth factor bioavailablity by genetic and proteolytic mechanisms, *J. Biol. Chem.,* 267:26031–26037 (1992).

Houck et al., "The vascular endothelial growth family: identification of a fourth molecular species and characterization of alternative splicing of RNA", *Mol. Endo.* 5:1806–1814 (1991).

Keck et al., "Disulfide Structure of the Heparin Binding Domain in Vascular Endothelial Growth Factor: Characterization of Posttranslational Modifications in VEGF", *Archiv. Biochem. Biophys.* 344:103–113 (1997).

Keck et al., "Vascular permeability factor, and endothelial cell mitogen related to PDGF."; *Science* 246:1309–1312 (1989).

Kelly and Hynes, "Transformation of Aspergillus niger by the amdS gene of Aspergillus nidulans", *EMBO J.* 4:475–479 (1985).

Kendall and Thomas. "Inhibition of vascular endothelial cell growth factor activity by an endogenously encoded soluble receptor", *PNAS USA* 90:10705–10709 (1993).

Keyt et al., "The carboxyl–terminal domain of vascular endothelial growth factor is critical for its mitogenic potency", *J. Biol. Chem. 271:*7788–7795 (1996).

Kim et al., "Inhibition of vascular endothelial growth factor–induced angiogenesis suppresses tumor growth in vivo", *Nature* 362:841–844 (1993).

Kondo et al., "The shortest isoform of human vascular endothelial growth factor/vascular permeability factor (VEGF/VPF$_{121}$) produced by *Saccharomyces cerevisiae* promotes both angiogenesis and vascular permeability", *Biochim. Biophys. Acta,* 1243:195–202 (1995).

Koolwijk et al., "Cooperative effect of tumor necrosis factor a and angiogenic growth factors on the formation of tubular structures of human microvascular endothelial cells in a three–dimensional fibrin matrix. Role of pericellular urokinase activity", *J. Cell Biol. 132:* 1177–1188 (1996).

Korz et al., "Simple fed–batch technique for high cell density cultivation of *Escherichia coli", J. Bacteriol, 39:*59–65, (1995).

Kruse, et al., "Two distinct functional sites of human interleukin 4 are identified by variants impaired in either receptor binding or receptor activation", EMBO J. 12, 5121–5129 (1993).

Leung et al. "Vascular endothelial growth factor is a secreted angiogenic mitogen."; *Science* 246:1306–1309 (1989).

Miller et al., "Gene Transfer Vectors for Mammalian Cells"ed. *Current Communications in Molecular Biology* (1987).

Mohanraj et al., "A Novel Method to Purify Recombinant Vascular Endothelial Growth Factor (VEGF121) Expressed in Yeast", *Biochem. Biophys. Res. Comm.* 215:750–756 (1995).

Muller, et al., "Vascular endothelial growth factor: Crystal structure and functional mapping of the kinase domain receptor binding site", *PNAS USA,* 94:7192–7197 (1997).

Mullis et al., "PCR: The polymerase Chain Reaction"ed. Birkhouser (1994).

Pepper et al., "Potent synergism between vascular endothelial growth factor and basic fibroblast growth factor in the induction of angiogenesis in vitro", *Biochem. Biophys. Res. Comm.*, 189:824–831 (1992).

Phillips et al., "Vascular endothelial growth factor (rhVEGF 165) stimulates direct angiogenesis in the rabbit cornea", *In Vivo* 8:961–965 (1995).

Plate et al., "Vascular endothelial growth factor is a potential tumor angiogenesis factor in human gliomas in vivo", *Nature* 359:845–848 (1992).

Plouët et al., "Isolation and characterization of a newly identified endothelial cell mitogen cell mitogen produced by AtT–20 cells", *EMBO J.* 8:3801–3806 (1989).

Proudfoot et al., "Extension of recombinant human RANTEs by the retention of the initiating methionine produces a potent antagonist", *J. Biol. Chem.*, 1996, 271:2599–2603.

Sambrook et al., *"Molecular Cloning: A Laboratory Manual,* second edition, Cold Spring Harbor Laboratory, Cold Spring Harbor", Sections 1.82, 16.32–16.37 (1989).

Siemeister et al., "The α–helical domain near the amino terminus is essential for dimerization of vascular endothelia growth factor", *J. Biol. Chem.* 273:11115–11120 (1989).

Siemeister et al., "Expression of Biologically Active Isoforms of the Tumor Angiogenesis Factor VEGF in *Escherichia coli*", *Biochem. Biophys. Res. Comm.* 222:249–255 (1996).

Soker et al. "Neuropilin–1 is expressed by endothelial and tumor cells as an isoform–specific receptor for vascular endothelial growth factor", *Cell* 92:735–745 (1998).

Soker et al., "Characterization of novel vascular endothelial growth factor (VEGF) receptors on tumor cells that bind VEGF165 via its exon 7–encoded domain", *J. Biol. Chem.* 271:5761–5767 (1996).

Tisher et al., "The human gene for vascular endothelial growth factor. Multiple protein forms are encoded through alternative exon splicing." *J. Biol. Chem.* 266:11947–11954 (1991).

Urlaub and Chasin, "Isolation of Chinese hamster cell mutants deficient in dihydrofolate reductase activity", *Proc. Natl. Acad. Sci. USA* 77:4216 (1980).

Vincenti et al., "Assignment of the Vascular Endothelial Growth Factor (VEGF) Gene to Human Chromosome 6p21.3", *Circulation* 93:1493–1495 (1996).

Wagner and Hynes, "Domain structure of fibronectin and its relation to function. Disulfides and sulfhydryl groups", *J. Biol. Chem.* 254:6746–6754 (1979).

Waltenberger et al., "Different signal transduction properties of KDR and Fit1, two receptors for vascular endothelial growth factor", *J. Biol. Chem.* 269:26988–26995 (1994).

Wang and Hanson *"Parenteral Formulations of Proteins and Peptides: Stability and Stabilizers", Journal of Parenteral Science and Technology,* Technical Report No. 10, Supp. 42–2S (1988).

Weir and Blackwell, eds., "Handbook of Experimental Immunology" 4th Edition, Blackwell Scientific Publications (Oxford) (1986).

Yang et al., "Substantially attenuated hemodynamic responses to *Escherichia coli*–derived vascular endothelial growth factor given by intravenous infusion compared with bolus injection", *J. Pharmacol. Exp. Ther.,* 284:103–10 (1998).

* cited by examiner hVEGF121

ATGAACTTTCTGCTGTCTTGGGTGCATTGGAGCCTTGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAATGTGACAAGCCGAGGCGGTGA

FIG. 2 hVEGF121

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKCDKPRR

FIG. 3 hVEGF145

ATGAACTTTCTGCTGTCTTGGGTGCATTGGAGCCTTGCCTTGCTGCTCTACCTCCACCATGCCAAGTG
GTCCCAGGCTGCACCCATGGCAGAAGGAGGAGGGCAGAATCATCACGAAGTGGTGAAGTTCATGGAT
GTCTATCAGCGCAGCTACTGCCATCCAATCGAGACCCTGGTGGACATCTTCCAGGAGTACCCTGATGA
GATCGAGTACATCTTCAAGCCATCCTGTGTGCCCCTGATGCGATGCGGGGGCTGCTGCAATGACGAG
GGCCTGGAGTGTGTGCCCACTGAGGAGTCCAACATCACCATGCAGATTATGCGGATCAAACCTCACCA
AGGCCAGCACATAGGAGAGATGAGCTTCCTACAGCACAACAAATGTGAATGCAGACCAAAGAAAGATA
GAGCAAGACAAGAAAAAAAATCAGTTCGAGGAAAGGGAAAGGGGCAAAAACGAAAGCGCAAGAAATC
CCGGTATAAGTCCTGGAGCGTATGTGACAAGCCGAGGCGGTGA

FIG. 4 hVEGF145

APMAEGGGQNHHEVVKFMDVYQRSYCHPIETLVDIFQEYPDEIEYIFKPSCVPLMRCGGCCNDEGLECV
PTEESNITMQIMRIKPHQGQHIGEMSFLQHNKCECRPKKDRARQEKKSVRGKGKGQKRKRKKSRYKSW
SVCDKPRR

FIG. 5 hVEGF 165

```
ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAATCCCTGTGGGCCTTGCTCAGAGCGGAGAAAGCA
TTTGTTTGTACAAGATCCGCAGACGTGTAAATGTTCCTGCAAAAACACAGACTCGCGTTGCAAGG
CGAGGCAGCTTGAGTTAAACGAACGTACTTGCAGATGTGACAAGCCGAGGCGGTGA
```

FIG. 6 hVEGF165

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQENPCGPCSERRKHLFVQDPQTCKCSCKNTDSRCKARQLELNERTCRCDKPRR

FIG. 7 hVEGF189

```
ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAAAATCAGTTCGAGGAAAGGGAAGGGGCAAAA
ACGAAAGCGCAAGAAATCCCGGTATAAGTCCTGGAGCGTGGGGCCTTGCTCAGAGCGGAGAAAGC
ATTTGTTTGTACAAGATCCGCAGACGTGTAAATGTTCCTGCAAAAACACAGACTCGCGTTGCAAG
GCGAGGCAGCTTGAGTTAAACGAACGTACTTGCAGATGTGACAAGCCGAGGCGGTGA
```

FIG. 8 hVEGF189

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVPCGPCSERRKHLFVQDPQTCKCSCKNTDSR
CKARQLELNERTCRCDKPRR

FIG. 9 hVEGF 206

```
ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAAAAATCAGTTCGAGGAAAGGGAAAGGGGCAAAA
ACGAAAGCGCAAGAAATCCCGGTATAAGTCCTGGAGCGTGTACGTTGGTGCCCGCTGCTGTCTAA
TGCCCTGGAGCCTCCCTGGCCCCCATCCCTGTGGGCCTTGCTCAGAGCGGAGAAAGCATTTGTTT
GTACAAGATCCGCAGACGTGTAAATGTTCCTGCAAAAACACAGACTCGCGTTGCAAGGCGAGGCA
GCTTGAGTTAAACGAACGTACTTGCAGATGTGACAAGCCGAGGCGGTGA
```

FIG. 10 hVEGF206

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVYVGARCCLMPWSLPGPHPCGPCSERRKHLF
VQDPQTCKCSCKNTDSRCKARQLELNERTCRCDKPRR.

FIG. 11 hVEGF110

APMAEGGGQNHHEVVKFMDVYQRSYCHPIETLVDIFQEYPDEIEYIFKPSCVPLMRCGGCCNDEG
LECVPTEESNITMQIMRIKPHQGQHIGEMSFLQHNKCECRPKKDR

FIG. 12

VASCULAR ENDOTHELIAL GROWTH FACTOR VARIANTS

RELATED APPLICATIONS

This application is a divisional of application Ser. No. 09/574,708, filed May 18, 2000, now U.S. Pat. No. 6,475,796, which claims the benefit of priority to application Ser. No. 60/135,312, filed May 20, 1999, both of which are hereby incorporated by reference in their entirety.

BACKGROUND OF THE INVENTION

I. Field of the Invention

This invention is directed to a method of enhancing the biological activity of vascular endothelial growth factors (VEGF). The invention further concerns certain VEGF variants having enhanced biological activity. The invention also concerns methods and means for preparing these variants, and pharmaceutical compositions comprising them. The invention further concerns methods of treatment using, and articles of manufacture containing such VEGF variants.

II. Description of Background and Related Art

Vascular endothelial growth factor (VEGF), also referred to as vascular permeability factor (VPF), is a secreted protein generally occurring as a homodimer and having multiple biological functions. The native human VEGF monomer occurs as one of five known isoforms, consisting of 121, 145, 165, 189, and 206 amino acid residues in length after removal of the signal peptide. The corresponding homodimer isoforms are generally referred to as $hVEGF_{121}$, $hVEGF_{145}$, $hVEGF_{165}$, $hVEGF_{189}$, and $hVEGF_{206}$, respectively. The known isoforms are generated by alternative splicing of the RNA encoded by a single human VEGF gene that is organized in eight exons, separated by seven introns, and has been assigned to chromosome 6p21.3 (Vincenti et al., *Circulation* 93:1493–1495 [1996]). A schematic representation of the various forms of VEGF generated by alternative splicing of VEGF mRNA is shown in FIG. 1, where the protein sequences encoded by each of the eight exons of the VEGF gene are represented by numbered boxes. $VEGF_{165}$ lacks the residues encoded by exon 6, while $VEGF_{121}$ lacks the residues encoded by exons 6 and 7. With the exception of $hVEGF_{121}$, all VEGF isoforms bind heparin. The lack of a heparin-binding region in $hVEGF_{121}$ is believed to have a profound effect on its biochemical properties. In addition, proteolytic cleavage of hVEGF produces a 110-amino acid species ($hVEGF_{110}$).

$hVEGF_{121}$ and $hVEGF_{165}$ are the most abundant of the five known isoforms. They both bind to the receptors KDR/Flk-1 and Flt-1 but $hVEGF_{165}$ additionally binds to a more recently discovered receptor ($VEGF_{165}R$) (Soker et al., *J. Biol. Chem.* 271:5761–5767 [1996]). $VEGF_{165}R$ has been recently cloned by Soke et al., and shown to be equivalent to a previously-defined protein known as neuropilin-1 (*Cell* 92:735–745 [1998]). The binding of $hVEGF_{165}$ to the latter receptor is mediated by the exon-7 encoded domain, which is not present in $hVEGF_{121}$.

VEGF is a potent mitogen for micro- and macrovascular endothelial cells derived from arteries, veins, and lymphatics, but shows significant mitogenic activity for virtually no other normal cell types. The denomination of VEGF reflects this narrow target cell specificity. VEGF has been shown to promote angiogenesis in various in vivo models, including, for example, the chick chorioallantoic membrane (Leung et al., *Science* 246:1306–1309 [1989]; Plouet et al., *EMBO J* 8:3801–3806 [1989]); the rabbit cornea (Phillips et al., *In Vivo* 8:961–965 [1995]); the primate iris (Tolentino et al, *Arch Opthalmol* 114:964–970 [1996]); and the rabbit bone (Connolly et al, *J. Clin. Invest.* 84:1470–1478 [1989]). As a result of its pivotal role in angiogenesis (spouting of new blood vessels) and vascular remodeling (enlargement of preexisting vessels), VEGF is a promising candidate for the treatment of coronary artery disease and peripheral vascular disease. High levels of VEGF are expressed in various types of tumors in response to tumor-induced hypoxia (Dvorak et al., *J. Exp. Med.* 174:1275–1278 [1991]; Plate et al., *Nature* 359:845–848 [1992]), and tumor growth has been inhibited by anti-VEGF antibodies and soluble VEGF receptors (Kim et al, *Nature* 362:841–844 [1993]; Kendall and Thomas, *PNAS USA* 90:10705–10709 [1993]).

The biologically active form of $hVEGF_{121}$ is a homodimer (in which the two chains are oriented anti-parallel) containing one N-linked glycosylation site per monomer chain at amino acid position 75 (Asn-75), which corresponds to a similar glycosylation site at position 75 of $hVEGF_{165}$. If the N-linked glycosylation structures are removed, the biologically active molecule has a molecular weight of about 28 kDa with a calculated pI of 6.1. Each monomer chain in the $hVEGF_{121}$ homodimer has a total of nine cysteines, of which six are involved in the formation of three intra-chain disulfides stabilizing the monomeric structure, two are involved in two inter-chain disulfide bonds stabilizing the dimeric structure, while until recently one cysteine (Cys-116) has been believed to remain unpaired. Recently, a Cys(116)-Cys(116) inter-chain disulfide bond has been reported in *E. coli* derived recombinant $hVEGF_{121}$ (Keck et al., *Arch. Biochem. Biophys.* 344:103–113 [1997]), and there are data indicating that $VEGF_{121}$ as produced in nature, also occurs in the form of homodimers that have the cysteines at positions 116 disulfide-bonded with each other. EP 0 484 401 describes the substitution of one or more cysteine residues, including Cys-116, within the native VEGF molecule by another amino acid, to render the molecule more stable.

SUMMARY OF THE INVENTION

The present invention concerns methods and means for enhancing the biological activity of vascular endothelial growth factor (VEGF), new VEGF variants with enhanced biological activity, and various uses of such new variants.

In a specific aspect, the invention concerns a method of enhancing the biological activity of a VEGF originally having a cysteine (C) residue at a position corresponding to amino acid position 116 of the 121 amino acids long native mature human VEGF ($hVEGF_{121}$) by removing such cysteine (C) residue to produce a VEGF variant. The variant preferably comprises a glycosylation site at a position corresponding to amino acid positions 75–77 of $hVEGF_{121}$, which is altered or removed, preferably by amino acid substitution within the glycosylation site to which the glycosylation would normally attach, so that glycosylation can no longer occur.

In another aspect, the invention concerns a variant of a native VEGF that originally has a cysteine (C) residue at amino acid position 116 and a glycosylation site at amino acid positions 75–77, comprising the substitution of said cysteine (C) by another amino acid and having the glycosylation site altered or removed, wherein the amino acid numbering follows the numbering of the 121 amino acids long native human VEGF ($hVEGF_{121}$), and wherein the variant has enhanced biological activity compared to hVEGF$_{121}$. The invention also concerns nucleic acid encoding such VEGF variants, a vector comprising the nucleic acid, cells transformed with such vector, and method for making the novel VEGF variants.

In yet another aspect, the invention concerns a composition comprising a VEGF variant having a cysteine (C) residue at amino acid position 116 substituted by another amino acid, and a glycosylation site at amino acid positions 75–77 altered or removed, wherein the amino acid numbering follows the numbering of the 121 amino acids long native human VEGF (hVEGF$_{121}$).

In a further aspect, the invention concerns a method of inducing angiogenesis and/or vascular remodeling by administering to a patient in need a VEGF variant having a cysteine (C) residue at amino acid position 116 substituted by another amino acid, and a glycosylation site at amino acid positions 75–77 altered or removed, wherein the amino acid numbering follows the numbering of the 121 amino acids long native human VEGF (hVEGF$_{121}$). In a particular embodiment, this method concerns the treatment of coronary artery disease or peripheral vascular disease.

In a still further aspect, the invention concerns a method for the prevention or repair of injury to blood vessels by administering an effective amount of a VEGF variant having a cysteine (C) residue at amino acid position 116 substituted by another amino acid, and a glycosylation site at amino acid positions 75–77 altered or removed, wherein the amino acid numbering follows the numbering of the 121 amino acids long native human VEGF (hVEGF$_{121}$). In a particular embodiment, the injury is associated with microvascular angiopathy, such as thrombotic microangiopathy (TMA). In a further embodiment, the invention concerns the treatment of microvascular angiopathy, e.g. TMA of the kidney, heart, or lungs. In a particularly preferred embodiment, the invention concerns the prevention or repair of injury to blood vessels in association with hemolytic uremic syndrome (HUS), including thrombotic thrombocytopenic purpura (TTP).

In another aspect, the invention concerns a method for the treatment of essential hypertension by administering an effective amount of a VEGF variant having a cysteine (C) residue at amino acid position 116 substituted by another amino acid, and a glycosylation site at amino acid positions 75–77 removed, wherein the amino acid numbering follows the numbering of the 121 amino acids long native human VEGF (hVEGF$_{121}$).

In a different aspect, the invention concerns an article of manufacture comprising a VEGF variant as hereinbefore defined, a container, and a label or package insert with instructions for administration.

In all embodiments, the VEGF variant preferably is N75Q,C116S hVEGF$_{121}$.

BRIEF DESCRIPTION OF THE DRAWINGS

FIG. 2 shows a nucleotide sequence encoding native human VEGF$_{121}$ (SEQ ID NO: 1).

FIG. 3 shows the amino acid sequence of native human VEGF$_{121}$ (SEQ ID NO: 2).

FIG. 4 shows a nucleotide sequence encoding native human VEGF$_{145}$ (SEQ ID NO: 3).

FIG. 5 shows the amino acid sequence of native human VEGF$_{145}$ (SEQ ID NO: 4).

FIG. 6 shows a nucleotide sequence encoding native human VEGF$_{165}$ (SEQ ID NO: 5).

FIG. 7 shows the amino acid sequence of native human VEGF$_{165}$ (SEQ ID NO: 6).

FIG. 8 shows a nucleotide sequence encoding native human VEGF$_{189}$ (SEQ ID NO: 7).

FIG. 9 shows the amino acid sequence of native human VEGF$_{189}$ (SEQ ID NO: 8).

FIG. 10 shows a nucleotide sequence of native human VEGF$_{206}$ (SEQ ID NO: 9).

FIG. 11 shows the amino acid sequence of native human VEGF$_{206}$ (SEQ ID NO: 10).

FIG. 12 shows the amino acid sequence of native human VEGF$_{10}$ (SEQ ID NO: 11).

DETAILED DESCRIPTION OF THE INVENTION

I. Definitions

Figure 1:
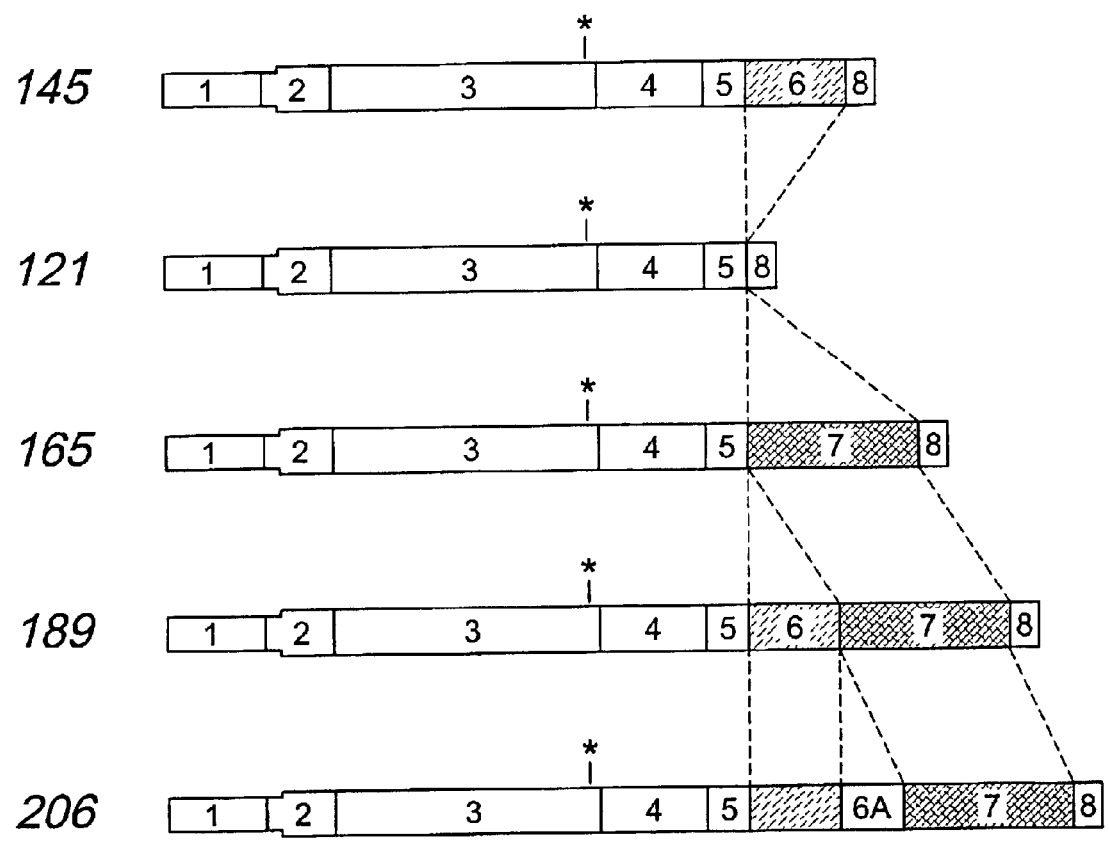
FIG. 1 is a schematic representation of the various forms of VEGF that can be encoded by alternative splicing of VEGF mRNA. The protein sequences encoded by each of the eight exons of the VEGF gene are represented by numbered boxes. The sequences encoded by exons 6 and 7 are rich in basic amino acid residues and confer the ability to interact with heparin and heparin-like molecules. Asterisks indicate N-linked glycosylation sites. Exon 1 and the first part of exon 2 (depicted by a narrower bar) encode the secretion signal sequence for the protein.

The term "vascular endothelial growth factor" or "VEGF" as used herein refers to any naturally occurring (native) forms of a VEGF polypeptide (also known as "vascular permeability factor" or "VPF") from any animal species, including humans and other mammalian species, such as murine, rat, bovine, equine, porcine, ovine, canine, or feline, and functional derivatives thereof. "Native human VEGF" consists of two polypeptide chains generally occurring as homodimers. Each monomer occurs as one of five known isoforms, consisting of 121, 145, 165, 189, and 206 amino acid residues in length. The homodimers produced from these isoforms will be hereinafter referred to as hVEGF$_{121}$, hVEGF$_{145}$, hVEGF$_{165}$, hVEGF$_{189}$, and hVEGF$_{206}$, respectively. Similarly to the human VEGF, "native murine VEGF" and "native bovine VEGF" are also known to exist in several isoforms, usually occurring as homodimers, with the monomer subunits extending 120, 164, and 188 amino acids in length. With the exception of hVEGF$_{121}$, all native human VEGF polypeptides are basic, heparin-binding molecules. hVEGF$_{121}$ is a weakly acidic polypeptide that does not bind to heparin. The term "VEGF" specifically includes VEGF-B, VEGF-C (also known as VRP), and VEGF-D (also known as zvegf2), all of which contain a cysteine corresponding to Cys116 of $VEGF_{121}$ (see, for example, Achen et al., *Proc. Natl. Acad. Sci.* 95:548–553 [1998], FIG. 1; and PCT Publication No. WO 98/24811). These and similar native forms, whether known or hereinafter discovered are all included in the definition of "native VEGF" or "native sequence VEGF", regardless of their mode of preparation, whether isolated from nature, synthesized, produced by methods of recombinant DNA technology, or any combination of these and other techniques. The term "vascular endothelial growth factor" or "VEGF" includes VEGF polypeptides in monomeric, homodimeric and heterodimeric forms. The definition of "VEGF" also includes a 110 amino acids long human VEGF species ($hVEGF_{110}$), and its homologues in other mammalian species, such as murine, rat, bovine, equine, porcine, ovine, canine, or feline, and functional derivatives thereof. In addition, the term "VEGF" covers chimeric, dimeric proteins, in which a portion of the primary amino acid structure corresponds to a portion of either the A-chain subunit or the B-chain subunit of platelet-derived growth factor, and a portion of the primary amino acid structure corresponds to a portion of vascular endothelial growth factor. In a particular embodiment, a chimeric molecule is provided consisting of one chain comprising at least a portion of the A- or B-chain subunit of a platelet-derived growth factor, disulfide linked to a second chain comprising at least a portion of a VEGF molecule. More details of such dimers are provided, for example, in U.S. Pat. Nos. 5,194,596 and 5,219,739 and in European Patent EP-B 0 484 401, the disclosures of which are hereby expressly incorporated by reference. The nucleotide and amino acid sequences of $hVEGF_{121}$, and bovine $VEGF_{120}$ are disclosed, for example, in U.S. Pat. Nos. 5,194,596 and 5,219,739, and in EP 0 484 401. $hVEGF_{145}$ is described in PCT Publication No. WO 98/10071; $hVEGF_{165}$ is described in U.S. Pat. No. 5,332,671; $hVEGF_{189}$ is described in U.S. Pat. No. 5,240,848; and $hVEGF_{206}$ is described in Houck et al. *Mol. Endocrinol.* 5:1806–1814 (1991). For the disclosure of the nucleotide and amino acid sequences of various human VEGF isoforms see also Leung et al., *Science* 246:1306–1309 (1989); Keck et al., *Science* 246:1309–1312 (1989); Tisher et al., *J. Biol. Chem.* 266:11947–11954 (1991); EP 0 370 989; and PCT publication WO 98/10071. Forms of VEGF are shown schematically in FIG. 1. FIGS. 2–12 (SEQ ID Nos: 1–11) show the nucleotide and amino acid sequences of various VEGF species.

A "functional derivative" of a native polypeptide is a compound having a qualitative biological activity in common with the native polypeptide. A functional derivative of a VEGF is a compound that has a qualitative biological activity in common with a native sequence (human or non-human) VEGF molecule as hereinabove defined. "Functional derivatives" include, but are not limited to, fragments of native polypeptides from any animal species (including humans), and derivatives of native (human and non-human) polypeptides and their fragments, provided that they have a biological activity in common with a corresponding native polypeptide. "Fragments" comprise regions within the sequence of a mature native VEGF polypeptide.

The term "derivative" is used to define amino acid sequence and glycosylation variants, and covalent modifications of a native polypeptide, whereas the term "variant" refers to amino acid sequence and glycosylation variants within this definition.

In general, the term "ammo acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In addition to the alterations at amino acid positions 116 and/or 75, the VEGF variants of the present invention may contain further amino acid alterations, including substitutions and/or insertions and/or deletions in any other region of the VEGF molecule, including the N- and C-terminal regions. The amino acid sequence variants of the present invention show at least about 75%, more preferably at least about 85%, even more preferably at least about 90%, most preferably at least about 95% amino acid sequence identity with a native sequence VEGF polypeptide.

"Sequence identity", is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389–3402. The parameters are set to default values, with the exception of the Penalty for mismatch, which is set to −1.

The term "glycosylation variant" is used to refer to a polypeptide having a glycosylation profile different from that of a corresponding native polypeptide. Glycosylation of polypeptides is typically either N-linked or O-linked. N-linked refers to the attachment of the carbohydrate moiety to the side of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved m O-linked glycosylation. Any difference in the location and/or nature of the carbohydrate moieties present in a variant or fragment as compared to its native counterpart is within the scope herein.

The glycosylation pattern of native polypeptides can be determined by well known techniques of analytical chemistry, including HPAE chromatography (Hardy, M. R. et al, *Anal. Biochem.* 170:54–62 [1988]), methylation analysis to determine glycosyl-linkage composition (Lindberg, B., *Meth. Enzymol.* 28:178–195 [1972]; Waeghe, T. J. et al., *Carbohydr. Res.* 123:281–304 [1983]), NMR spectroscopy, mass spectrometry, etc.

"Covalent derivatives" include modifications of a native polypeptide or a fragment thereof with an organic proteinaceous or non-proteinaceous derivatizing agent, and post-translational modifications. Covalent modifications are traditionally introduced by reacting targeted ammo acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the trk receptor polypeptides of the present invention. Other post-translational modifications include hydroxylation of proline and lysine, phosphorylation of hydroxyl groups of seryl, tyrosine or threonyl residues, methylation of the .alpha.-amino groups of lysine, arginine, and histidine side chains (T. E. Creighton, Proteins: Structure and Molecular Properties, W.H. Freeman & Co., San Francisco, pp. 79–86 [1983]).

The term "glycosylation site" is used to refer to an N-linked glycosylation that requires a tripeptidyl sequence of the formula Asp-X-Ser or Asp-X-Thr, wherein X is any amino acid other than proline (Pro), which prevents glycosylation.

The terms "biological activity" and "activity" in connection with the VEGF variants of the present invention mean mitogenic activity as determined in any in vitro assay of endothelial cell proliferation. Activity is preferably determined in a human umbilical vein endothelial (HUVE) cell-based assay, as described, for example, in any of the following publications: Gospodarowicz et al., *PNAS USA* 86, 7311–7315 (1989); Ferrara and Henzel, *Biochem. Biophys. Res. Comm.* 161:851–858 (1989); Conn et al., *PNAS USA* 87:1323–1327 (1990); Soker et al., *Cell* 92:735–745 (1998); Waltenberger et al, *J. Biol. Chem.* 269:26988–26995 (1994); Siemeister et al., Biochem. Biophys. Res. Comm. 222:249–255 (1996); Fiebich et al, *Eur. J. Biochem.* 211:19–26 [1993]; Cohen et al, *Growth Factors* 7:131–138 (1993). A particular HUVE cell (HUVEC) assay is described in the examples below.

The terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Under transcriptional control" is a term well-understood in the art and indicates that transcription of a polynucleotide sequence, usually a DNA sequence, depends on its being operably (operatively) linked to an element which contributes to or promotes transcription.

A "host cell" includes an individual cell or cell culture which can be or has been a recipient of any vector of this invention Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, cats, cattle, horses, sheep, pigs, etc. Preferably, the mammal is human.

An "effective amount" is an amount sufficient to effect beneficial or desired clinical results. An effective amount can be administered in one or more administrations. For purposes of this invention, an effective amount of a VEGF variant is an amount that is sufficient to palliate, ameliorate, stabilize, reverse, slow or delay the progression of the disease state. In a preferred embodiment of the invention, the "effective amount" is defined as an amount capable of stimulating the growth and/or remodeling of collateral blood vessels. In another preferred embodiment, the "effective amount" is defined as an amount capable of preventing, reducing or reversing endothelial cell injury or injury to the surrounding tissues.

"Repair" of injury includes complete and partial repair, such as reduction of the injury that has already occurred, or partial reinstatement of the functionality of a tissue of organ.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

Administration "m combination with" one or more further therapeutic agents includes simultaneous (concurrent) and consecutive administration in any order.

"Angiogenesis" is defined the promotion of the growth of new blood capillary vessels from existing endothelium, while "therapeutic angiogenesis" is defined as the promotion of the growth or new blood vessels and/or demodeling of old blood vessels, for example, to increase blood supply to an ischemic region.

The term "peripheral arterial disease" also known as "peripheral vascular disease", is defined as the narrowing or obstruction of the blood vessels supplying the extremities. It is a common manifestation of atherosclerosis, and most often affects the blood vessels of the leg. Two major types of peripheral arterial disease are intermittent claudication, in which the blood supply to one or more limbs has been reduced to the point where exercise cannot be sustained without the rapid development of cramping pain; and critical leg ischemia, in which the blood supply is no longer sufficient to completely support the metabolic needs of even the resting limb.

"Coronary artery disease" is defined as the narrowing or obstruction of one or more of the arteries that supply blood to the muscle tissue of the heart. This disease is also a common manifestation of atherosclerosis.

The term "microvascular angiopathy" is used to describe acute injuries to smaller blood vessels and subsequent dysfunction of the tissue in which the injured blood vessels are located. Microvascular angiopathies are a common feature of the pathology of a variety of diseases of various organs, such as kidney, heart, and lungs. The injury is often associated with endothelial cell injury or death and the presence of products of coagulation or thrombosis. The agent of injury may, for example, be a toxin, an immune factor, an infectious agent, a metabolic or physiological stress, or a component of the humoral or cellular immune system, or may be as of yet unidentified. A subgroup of such diseases is unified by the presence of thrombotic microangiopathies (TMA), and is characterized clinically by non-immune hemolytic anemia, thrombocytopenia, and/or renal failure. The most common cause of TMA is the hemolytic uremic syndrome (HUS), a disease that is particularly frequent in childhood, where it is the most common cause of acute renal failure. The majority of these cases are associated with enteric infection with the verotoxin producing strain, E. coli O157. Some HUS patients, especially adults, may have a relative lack of renal involvement and are sometimes classified as having thrombotic thrombocytopenic purpura (TTP). However, thrombotic microangiopathies may also occur as a complication of pregnancy (eclampsia), with malignant hypertension following radiation to the kidney, after transplantation (often secondary to cyclosporine or FK506 treatment), with cancer chemotherapies (especially mitomycin C), with certain infections (e.g., Shigella or HIV), in association with systemic lupus or the antiphospholipid syndrome, or may be idiopathic or familial. Experimental data suggest that endothelial cell injury is a common feature in the pathogenesis of HUS/TTP. See, e.g. Kaplan et al., *Pediatr. Nephrol.* 4:276 (1990). Endothelial cell injury triggers a cascade of subsequent events, including local intravascular coagulation, fibrin deposition, and platelet activation and aggregation. The mechanisms that mediate these events are not well understood. In the case of verotoxin-mediated HUS, injury to the endothelium leads to detachment and death, with local platelet activation and consumption, fibrin deposition and microangiopathic hemolysis.

The phrase "hemolytic-uremic syndrome" or "HUS" is used in the broadest sense, and includes all diseases and conditions characterized by thrombotic microangiopathic hemolytic anemia and variable organ impairment, irrespective of whether renal failure is the predominant feature. Although, as mentioned before, the disease is particularly frequent in childhood, the term "HUS" specifically covers a syndrome, typically observed in adults, that is also referred to as thrombotic thrombocylopenic purpura (TTP) and is generally characterized by the predominance of thrombocytopenia and neurologic impairment, but has thrombotic microangiopathy as the underlying pathologic lesion.

The terms "amino acid" and "amino acids" refer to all naturally occurring L-α-amino acids. This definition is meant to include norleucine, ornithine, and homocysteine. The amino acids are identified by either the single-letter or three-letter designations, as follows:

Asp (D) aspartic acid
Thr (T) threonine
Ser (S) serine
Glu (E) glutamic acid
Pro (P) proline
Gly (G) glycine
Ala (A) alanine
Cys (C) cysteine
Val (V) valine
Met (M) methionine
Ile (I) isoleucine
Leu (L) leucine
Tyr (Y) tyrosine
Phe (F) phenylalanine
His (H) histidine
Lys (K) lysine
Arg (R) arginine
Trp (W) tryptophan
Gln (Q) glutamine
Asn (N) asparagine The notations throughout this application describe VEGF amino acid sequence variants, where the location of a particular amino acid residue in the polypeptide chain of VEGF is identified by a number, following the amino acid numbering of $hVEGF_{121}$. In the present application, similarly positioned residues in the VEGF variants are designated by these numbers, even though the actual residue is not so numbered due to deletions or insertions in the molecule. This will occur, for example, in the case of variants which, in addition to the specified amino acid substitutions, contain further deletion(s) and/or insertion(s). Substituted VEGF variants are designated by identifying the native (wild-type) amino acid on the left side of the number denoting the position where the substitution takes place, and identifying the substituted amino acid on the right side of the number. For example, replacement of the amino acid asparagine (N) with a glutamine (Q) at position 75 of $hVEGF_{121}$ is designated N75Q $hVEGF_{121}$. The double mutant, additionally having cysteine (C) at position 116 replaced by serine (S) is designated N75Q, C116S $hVEGF_{121}$.

"Carriers" as used herein include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutanine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

II. General Methods

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

The methods of the present invention concern variants of a native sequence VEGF molecule ordinarily having a free cysteine (C) residue at a position corresponding to amino acid position 116 of the 121 amino acids long native mature human VEGF (hVEGF$_{121}$). It has been found that the elimination of this cysteine (C) residue produces VEGF variants that have an enhanced biological activity compared to native mature hVEGF$_{121}$. The cysteine residue is preferably replaced by another amino acid. Preferred amino acids used for substitution are serine, glycine, alanine, valine, leucine, isoleucine, threonine or methionine, more preferably serine, glycine or alanine, most preferably serine. Substitution is preferably performed by site-directed mutagenesis of the nucleic acid sequence encoding the unmodified variant, having a cysteine (C) at position 116. Particularly preferred is site-directed mutagenesis using polymerase chain reaction (PCR) amplification (see, for example, U.S. Pat. No. 4,683,195 issued Jul. 28, 1987; and Current Protocols In Molecular Biology, Chapter 15 (Ausubel et al., ed., 1991). Other site-directed mutagenesis techniques are also well known in the art and are described, for example, in the following publications: Current Protocols In Molecular Biology, supra, Chapter 8; Molecular Cloning: A Laboratory Manual., 2$^{nd}$ edition (Sambrook et al, 1989); Zoller et al., Methods Enzymol. 100:468–500 (1983); Zoller & Smith, DNA 3:479–488 (1984); Zoller et al., Nucl. Acids Res, 10.6487 (1987); Brake et al., Proc. Natl. Acad. Sci. USA 81:4642–4646 (1984); Botstein et al., Science 229:1193 (1985); Kunkel et al., Methods Enzymol. 154:367–82 (1987), Adelman et al, DNA 2:183 (1983); and Carter et al., Nucl. Acids Res., 13:4331 (1986). Cassette mutagenesis (Wells et al., Gene, 34:315 [1985]), and restriction selection mutagenesis (Wells et al., Philos. Trans. R. Soc. London SerA, 317:415 [1986]) may also be used.

VEGF variants with more than one ammo acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

In a preferred embodiment, the present invention involves the generation of VEGF variants that, in addition to the elimination of a free (unpaired) cysteine at position 116, have an N-linked glycosylation site removed at amino acid position 75. An N-linked glycosylation site may be a tripeptidyl sequence of the formula Asn-X-Ser or Asn-X-Thr, wherein Asn is the acceptor and X is any of the twenty genetically encoded amino acids except Pro, which is known to prevent glycosylation. In native hVEGF$_{121}$, an Asn-Ile-Thr (NIT) glycosylation site is present at amino acid positions 75–77. The removal of this glycosylation site is preferably achieved by amino acid substitution for at least one residue of the glycosylation signal. In a particularly preferred variant, Asn (N) at position 75 is replaced by Glu (Q). The substitution may be performed by any of the mutagenesis techniques discussed above.

DNA encoding the VEGF variants of the present invention may also be prepared by chemical synthesis. Methods of chemically synthesizing DNA having a specific sequence are well known in the art. Such techniques include the phosphoramidite method (Beaucage and Caruthers, Tetrahedron Letters 22:1859 [1981]; Matteucci and Caruthers, Tetrahedron Letters 21:719 [1980]; and Matteucci and Caruthers, J. Amer. Chem. Soc. 103: 3185 [1981]), and the phosphotriester approach (Ito et al., Nucleic Acids Res. 10:1755–1769 [1982]).

In addition to removing the underlying glycosylation site, the N-linked glycosylation at amino acid position 75 can be substantially removed by using an endoglycosidase, such as Endoglycosidase H (Endo-H), which is capable of (partial) removal of high mannose and hybrid oligosaccharides. Endo-H treatment is accomplished via techniques known per se, as described, for example, in Tarentino et al., J. Biol. Chem. 249: 811 (1974); Trimble et al, Anal. Biochem. 141:515 (1984); and Little et al., Biochem. 23:6191 (1984).

The cDNA encoding the desired VEGF variant of the present invention is inserted into a replicable vector for cloning and expression. Suitable vectors are prepared using standard techniques of recombinant DNA technology, and are, for example, described in the textbooks cited above. Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins.

The VEGF variants of the present invention can be expressed in eukaryotic hosts, such as eukaryotic microbes (yeast), cells isolated from multicellular organisms (mammalian cell cultures), plants and insect cells.

While prokaryotic host provide a convenient means to synthesize eukaryotic proteins, when made this fashion, proteins usually lack many of the immunogenic properties, three-dimensional conformation, glycosylation, and other features exhibited by authentic eukaryotic proteins. Eukaryotic expression systems overcome these limitations.

Yeasts are particularly attractive as expression hosts for a number of reasons. They can be rapidly growth on inexpensive (minimal) media, the recombinant can be easily selected by complementation, expressed proteins can be specifically engineered for cytoplasmic localization or for extracellular export, and are well suited for large-scale fermentation.

*Saccharomyces cerevisiae* (common baker's yeast) is the most commonly used among lower eukaryotic hosts. However, a number of other genera, species, and strains are also available and useful herein, such as *Pichia pastoris* (EP 183,070; Sreekrishna et al., *J. Basic Microbiol.* 28:165–278 [1988]). The expression of $hVEGF_{121}$ in *Saccharomyces cerevisiae* is disclosed, for example, by Kondo et al., *Biochim. Biophys. Acta* 1243:195–202 (1995), the entire disclosure of which is hereby expressly incorporated by reference. The variants of the present invention may be expressed in an analogous fashion. Expression of $hVEGF_{121}$ in Pichia pastoris has been described by Mohanraj et al, *Biochem. Biophys. Res. Commun.* 215:750–756 (1995), while similar expression of the $hVEGF_{165}$ molecule was described by Mohanraj et al., *Growth Factors* 12:17–27 (1995). The yeast expression system was purchased from Invitrogen (San Diego, Calif.). The disclosures of these references are hereby expressly incorporated by reference. Other yeasts suitable for VEGF expression include, without limitation, Kluyveromyces hosts (U.S. Pat. No. 4,943,529), e.g. *Kluyveromyces lactis; Schizosaccharomyces pombe* (Beach and Nurse, *Nature* 290:140 (1981); Aspergillus hosts, e.g. *A. niger* (Kelly and Hynes, *EMBO J.* 4:475–479 [1985]) and *A. nidulans* (Ballance et al, *Biochem. Biophys. Res. Commun.* 112:284–289 [1983]), and Hansenula hosts, e.g. *Hansenula polymorpha*.

Preferably a methylotrophic yeast is used as a host in performing the methods of the present invention. Suitable methylotrophic yeasts include, but are not limited to, yeast capable of growth on methanol selected from the group consisting of the genera Pichia and Hansenula. A list of specific species which are exemplary of this class of yeasts may be found, for example, in C. Anthony, *The Biochemistry of Methylotrophs*, 269 (1982). Presently preferred are methylotrophic yeasts of the genus Pichia such as the auxotrophic *Pichia pastoris* GS115 (NRRL Y-15851); *Pichia pastoris* GS190 (NRRL Y-18014) disclosed in U.S. Pat. No. 4,818,700; and *Pichia pastoris* PPF1 (NRRL Y-18017) disclosed in U.S. Pat. No. 4,812,405. Auxotrophic *Pichia pastoris* strains are also advantageous to the practice of this invention for their ease of selection. It is recognized that wild type *Pichia pastoris* strains (such as NRRL Y-11430 and NRRL Y-11431) may be employed with equal success if a suitable transforming marker gene is selected, such as the use of SUC2 to transform *Pichia pastoris* to a strain capable of growth on sucrose, or if an antibiotic resistance marker is employed, such as resistance to G418. *Pichia pastoris* lmear plasmids are disclosed, for example, in U.S. Pat. No. 5,665,600.

Suitable promoters used in yeast vectors include the promoters for 3-phosphoglycerate kinase (Hitzeman et al., *J. Biol. Chem.* 255:2073 [1980]); and other glycolytic enzymes (Hess et al., *J. Adv. Enzyme Res.* 7:149 [1968]; Holland et al., *Biochemistry* 17:4900 [1978]), e.g., enolase, glyceraldehyde-3-phosphate dehydrogenase, hexokinase, pyvurate decarboxylase, phosphofructokinase, glucose-6-phosphate isomerase, 3-phosphoglycerate mutase, pyruvate kinase, triosephosphate somerase, phosphoglucose isomerase, and glucokinase. In the constructions of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter regions for alcohol oxidase 1 (AOX1, particularly preferred for expression in *Pichia*), alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter and termination sequences, with or without an origin of replication, is suitable. Yeast expression systems are commercially available, for example, from Clontech Laboratories, Inc. (Palo Alto, Calif., e.g. pYEX 4T family of vectors for *S. cerevisiae*), Invitrogen (Carlsbad, Calif., e.g. pPICZ series Easy Select *Pichia* Expression Kit) and Stratagene (La Jolla, Calif., e.g. ESP™ M Yeast Protein Expression and Purification System for *S. pombe* and pESC vectors for *S. cerevisiae*). The production of N75Q, C116S $hVEGF_{121}$ in *P. pastoris* is described in detail in the Examples below. Other VEGF variants can be expressed in an analogous fashion.

Cell cultures derived from multicellular organisms may also be used as hosts to practice the present invention. While both invertebrate and vertebrate cell cultures are acceptable, vertebrate cell cultures, particularly mammalian cells, are preferable. Examples of suitable cell lines include monkey kidney CV1 cell line transformed by SV40 (COS-7, ATCC CRL 1651); human embryonic kidney cell line 293S (Graham et al, *J. Gen. Virol.* 36:59 [1977]); baby hamster kidney cells (BHK, ATCC CCL 10); Chinese hamster ovary (CHO) cells (Urlaub and Chasm, *Proc. Natl. Acad Sci. USA* 77:4216 [1980]; monkey kidney cells (CVI-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065).

Suitable promoters used in mammalian expression vectors are often of viral origin. These viral promoters are commonly derived from cytomeagolavirus (CMV), polyoma virus, Adenovirus2, and Simian Virus 40 (SV40). The SV40 virus contains two promoters that are termed the early and late promoters. They are both easily obtained from the virus as one DNA fragment that also contains the viral origin of replication (Fiers et al, *Nature* 273:113 [1978]). Smaller or larger SV40 DNA fragments may also be used, provided they contain the approximately 250-bp sequence extending from the HindIII site toward the BglI site located in the viral origin of replication. An origin of replication may be obtained from an exogenous source, such as SV40 or other virus, and inserted into the cloning vector. Alternatively, the host cell chromosomal mechanism may provide the origin of replication. If the vector containing the foreign gene is integrated into the host cell chromosome, the latter is often sufficient.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5"(Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

Prokaryotes are the preferred hosts for the initial cloning steps, and are particularly useful for rapid production of large amounts of DNA, for production of single-stranded DNA templates used for site-directed mutagenesis, for screening many mutants simultaneously, and for DNA sequencing of the mutants generated. Biologically active isoforms of hVEGF have been successfully expressed in *Escherichia coli* (*E. coli*), see, for example Siemeister et al, *Biochem. and Biophys. Res. Comm.* 222:249–255 (1996), where *E. coli* strain BL21 carrying an inducible T7 RNA polymerase gene (Studier et al., *Methods Enzymol.* 185:60–98 [1990]) was transformed with the appropriate constructs. Other *E. coli* strains suitable for the production of the VEGF variants of the present invention include, for example, AD494 (DE3); EB105; and CB (*E. coli*) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Prokaryotes, e.g. *E. coli*, produce the VEGF variants in an unglycosylated form, therefore, there is no need for the removal of the glycosylation signal at amino acid position 75.

Vectors used for transformation of prokaryotic host cells usually have a replication site, marker gene providing for phenotypic selection in transformed cells, one or more promoters compatible with the host cells, and a polylinker region containing several restriction sites for insertion of foreign DNA. Plasmids typically used for transformation of *E. coli* include pBR322, pUC18, pUC19, pUC118, pUC119, and Bluescript M13, all of which are commercially available and described in Sections 1.12–1.20 of Sambrook et al, supra. The promoters commonly used in vectors for the transformation of prokaryotes are the T7 promoter (Studier et al, supra); the tryptophan (trp) promoter (Goeddel et al. *Nature* 281:544 [1979]); the alkaline phosphatase promoter (phoA); and the β-lactamase and lactose (lac) promoter systems.

In *E. coli*, the VEGF variants typically accumulate in the form of inclusion bodies, and need to be solubilized, purified, refolded and dimerized. Methods for the recovery and refolding of VEGF isoforms from *E. coli* are described, for example, in Siemeister et al., supra.

Many eukaryotic proteins, including VEGF, contain an endogenous signal sequence as part of the primary translation product. This sequence targets the protein for export from the cell via the endoplasmic reticulum and Golgi apparatus. The signal sequence is typically located at the ammo terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the pre-protein, or the immature form of the protein, in contrast to the protein from which the signal sequence has been cleaved off, which is usually referred to as the mature protein. Proteins may also be targeted for secretion by linking a heterologous signal sequence to the protein. This is readily accomplished by ligating DNA encoding a signal sequence to the 5' end of the DNA encoding the protein, and expressing the fusion protein in an appropriate host cell. Prokaryotic and eukaryotic (yeast and mammalian) signal sequences may be used, depending on the type of the host cell. The DNA encoding the signal sequence is usually excised from a gene encoding a protein with a signal sequence, and then ligated to the DNA encoding the protein to be secreted, e.g. VEGF. Alternatively, the signal sequence can be chemically synthesized. The signal must be functional, i.e. recognized by the host cell signal peptidase such that the signal sequence is cleaved and the protein is secreted. A large variety of eukaryotic and prokaryotic signal sequences is known in the art, and can be used in performing the process of the present invention. Yeast signal sequences include, for example, acid phosphatase, alpha factor, alkaline phosphatase and invertase signal sequences. Prokaryotic signal sequences include, for example LamB, OmpA, OmpB and OmpF, MalE, PhoA, and β lactamase.

Mammalian cells are usually transformed with the appropriate expression vector using a version of the calcium phosphate method (Graham et al, *Virology* 52:546 [1978]; Sambrook et al., supra, sections 16.32–16.37), or, more recently, lipofection. However, other methods, e.g. protoplast fusion, electroporation, direct microinjection, etc. are also suitable.

Yeast hosts are generally transformed by the polyethylene glycol method (Hinnen, *Proc. Natl. Acad, Sci. USA* 75–1929 [1978]). Yeast, e.g. *Pichia pastoris*, can also be transformed by other methodologies, e.g. electroporation, as described in the Examples.

Prokaryotic host cells can, for example, be transformed using the calcium chloride method (Sambrook et al, supra, section 1.82), or electroporation.

If the host is *Pichia pastoris*, transformed cells can be selected for by using appropriate techniques including, but not limited to, culturing previously auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformant. Isolated transformed *Pichia pastoris* cells are cultured by appropriate fermentation techniques such as shake flask fermentation, high density fermentation or the technique disclosed by Cregg et al. in, High-Level h112Expression and Efficient Assembly of Hepatitis B Surface Antigen in: the Methylotrophic Yeast, *Pichia Pastoris*, *Bio/Technology* 5:479–485 (1987). Isolates may be screened by assaying for VEGF production to identify those isolates with the highest production level.

Transformed strains, that are of the desired phenotype and genotype, are grown in fermentors. For the large-scale production of recombinant DNA-based products in methylotrophic yeast, a three stage, high cell-density fed-batch fermentation system is normally the preferred fermentation protocol employed. In the first, or growth stage, expression hosts are cultured in defined minimal medium with an excess of a non-inducing carbon source (e.g. glycerol). When grown on such carbon sources, heterologous gene h114 expression is completely repressed, which allows the generation of cell mass in the absence of heterologous protein h115 expression. It is presently preferred, during this growth stage, that the pH of the medium be maintained at about 4.5–5. Next, a short period of non-inducing carbon source limitation growth is allowed to further increase cell mass and derepress the methanol responsive promoter. The pH of the medium during this limitation growth period is adjusted to the pH value to be maintained during the production phase, which is generally carried out at about pH 5 to about pH 6, preferably either about pH 5.0 or about pH 6.0. Subsequent to the period of growth under limiting conditions, methanol alone ("limited methanol fed-batch mode") or a limiting amount of non-inducing carbon source plus methanol (referred to herein as "mixed-feed fed-batch mode") is added in the fermentor, inducing the expression of the heterologous gene driven by a methanol responsive promoter. This third stage is the so-called production stage. Fermentation can also be conducted in shake flasks, essentially as described in the Examples.

More recently, techniques have been developed for the expression of heterologous proteins in the milk of non-human transgenic animals. For example, Krimpenfort et al, *Biotechnology* 9:844–847 (1991) describes microinjection of fertilized bovine oocytes with genes encoding human proteins and development of the resulting embryos in surrogate mothers. The human genes were fused to the bovine .alpha.S.sub.1 casein regulatory elements. This general technology is also described in PCT Application WO91/08216 published Jun. 13, 1991. PCT application WO88/00239, published Jan. 14, 1988, describes procedures for obtaining suitable regulatory DNA sequences for the products of the mammary glands of sheep, including beta lactoglobulin, and the construction of transgenic sheep modified so as to secrete foreign proteins in milk. PCT publication WO88/01648, published Mar. 10, 1988, generally describes construction of transgenic animals which secrete foreign proteins into milk under control of the regulatory sequences of bovine alpha lactalbumin gene. PCT application WO88/10118, published Dec. 29, 1988, describes construction of transgenic mice and larger mammals for the production of various recombinant human proteins in milk. Thus, techniques for construction of appropriate host vectors containing regulatory sequences effective to produce foreign proteins in mammary glands and cause the secretion of said protein into milk are known in the art.

Among the milk-specific protein promoters are the casein promoters and the beta lactoglobulin promoter. The casein promoters may, for example, be selected from an alpha casein promoter, a beta casein promoter or a kappa casein promoter. Preferably, the casein promoter is of bovine origin and is an alpha S-1 casein promoter. Among the promoters that are specifically activated in mammary is the long terminal repeat (LTR) promoter of the mouse mammary tumor virus (MMTV). The milk-specific protein promoter or the promoters that are specifically activated in mammary tissue may be derived from either cDNA or genomic sequences. Preferably, they are genomic in origin.

Signal peptides that are useful in expressing heterologous proteins in the milk of transgenic mammals include milk-specific signal peptides or other signal peptides useful in the secretion and maturation of eukaryotic and prokaryotic proteins. Preferably, the signal peptide is selected from milk-specific signal peptides or the signal peptide of the desired recombinant protein product, if any. Most preferably, the milk-specific signal peptide is related to the milk-specific promoter used in the expression system of this invention.

III. Pharmaceutical Compositions

Pharmaceutical compositions of the present invention can comprise a polynucleotide encoding a VEGF variant herein, or, alternatively, pharmaceutical compositions can comprise the VEGF variant itself.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Compositions comprising a VEGF variant or a polynucleotide encoding a VEGF variant can also be formulated as pharmaceutically acceptable salts (e.g., acid addition salts) and/or complexes thereof. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intra-arterial, intraperitoneal, intrapericardial, intracoronary, subcutaneous, and intramuscular, oral, topical, or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions comprising a VEGF variant or a polynucleotide encoding a VEGF variant can be formulated for a variety of modes of administration, including systemic and topical or localized administration. Techniques and formulations generally may be found in *Remington's Pharmaceutical Sciences*, 18th Edition, Mack Publishing Co., Easton, Pa. 1990. See, also, Wang and Hanson "*Parenteral Formulations of Proteins and Peptides Stability and Stabilizers*", *Journal of Parenteral Science and Technology*, Technical Report No. 10, Supp. 42–2S (1988). A suitable administration format can best be determined by a medical practitioner for each patient individually.

For systemic administration, injection is preferred, e g., intramuscular, intravenous, intra-arterial, intracoronary, intrapericardial, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (eg, propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5 6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

The VEGF variants of the present invention can also be introduced directly into the heart, by using a catheter inserted directly into a coronary artery, as described, for example, in U.S. Pat. No. 5,244,460.

Alternatively, the compounds can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol must. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, eg, a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg, preferably 0.05 and 20 mg/kg, most preferably 0.05 and 2 mg/kg of the individual to be treated.

For use by the physician, the compositions are provided in dosage unit form containing an amount of a VEGF variant herein.

IV. Therapeutic Targets

The VEGF variants of the present invention are promising candidates for the same indications as native sequence VEGF molecules. Accordingly, the VEGF variants herein can be used to induce angiogenesis and/or vascular remodeling, and therefore may find utility in the treatment of coronary artery disease and/or peripheral vascular disease. The VEGF variants of the present invention can be used, for example, to foster myocardial blood vessel growth and to improve blood flow to the heart (see, e.g. U.S. Pat. No. 5,244,460).

One of the main therapeutic targets of the present invention is the treatment of peripheral arterial disease and/or coronary artery disease. Both peripheral arterial disease and coronary artery disease can often be treated successfully with either angioplasty/endarterectomy approaches (to open up the blockage caused by atherosclerotic plaque growth) or surgical bypass (to create a conduit around the blockage). In a significant number of cases, however, patients are deemed to be poor risks to be helped by either of these types of approaches. It is this group of so-called "no option" patients that are expected to be the primary beneficiaries of the treatments provided by the present invention. It is foreseen that the new blood vessels, or newly-enlarged vessels, created in response to the treatment by the VEGF variants of the present invention, will create a natural bypass around the blocked vessels, without significant side-effects. As a result, the long-term hope is that this therapy will be used to replace angioplasty/endarterectomy/surgical bypass in the coronary artery disease patient population in general, or at least in some cases.

The present invention is further directed to the treatment (including prevention) of injury to blood vessels and to the treatment (including prevention) of injury to tissues containing such blood vessels, in conditions where the endothelial cell injury is mediated by known or unknown toxins, such as occurs in hemolytic uremic syndrome (HUS), toxic shock syndrome, exposure to venoms, or exposure to chemical or medicinal toxins, and in conditions where the endothelial cell injury is mediated by hypertension.

The invention further concerns the treatment (including prevention) of kidney diseases associated with injury to, or atrophy of, the vasculature of the glomerulus and interstitium.

The invention also concerns the treatment (including prevention) of injury to the endothelium of blood vessels, and for the treatment (including prevention) of injury to tissues containing such injured blood vessels in diseases associated with hypercoagulable states, platelet activation or aggregation, thrombosis, or activation of proteins of the clotting cascade, or in activation of coagulation or platelet aggregation such as preeclampsia, thrombotic thombocytopenic purpura (TTP), disseminated intravascular coagulation, sepsis, pancreatis.

The invention also provides methods for the treatment (including prevention) of injury to blood vessels or injury to the surrounding tissue adjacent to injured blood vessels arising as a result of diminished blood flow due to decreased blood pressure, or full or partial occlusion of the blood vessel, due to atherosclerosis, thrombosis, mechanical trauma, vascular wall dissection, surgical dissection, or any other impediment to normal blood flow or pressure. Specifically, the invention provides methods for the treatment (including prevention) of acute renal failure, myocardial infarction with or without accompanying thrombolytic therapy, ischemic bowel disease, transient ischemic attacks, and stroke.

The invention also provides methods for the treatment (including prevention) of hypoxia or hypercapnia or fibrosis arising from injury to the endothelium of the lungs occasioned by injurious immune stimuli, toxin, exposure, infection, or ischemia, including but not limited to acute respiratory distress syndrome, toxic alveolar injury, as occurs in smoke inhalation, pneumonia, including viral and bacterial infections, and pulmonary emboli.

The invention further provides methods and means for the treatment (including prevention) of pulmonary dysfunction arising from injury to the pulmonary endothelium, including disorders arising from birth prematurity, and primary and secondary causes of pulmonary hypertension.

The methods disclosed herein can also be used for the treatment of wounds arising from any injurious breach of the dermis with associated vascular injury.

The invention also provides methods for the treatment (including prevention) or injury to the endothelium and blood vessels, and for the treatment (including prevention) of injury to tissues containing injured blood vessels, due to injurious immune stimuli, such as immune cytokines, immune complexes, proteins of the complement cascade, including but not restricted to diseases such as vasculitis of all types, allergic reactions, diseases of immediate and delayed hypersensitivity, autoimmune diseases.

The methods of the present invention further useful in the preservation or enhancement of function of organ allografts, including but not restricted to transplants of kidney, heart, liver, lung, pancreas, skin, bone, intestine, and xenografts.

Specific kidney diseases that may be treatable by using the methods of the present invention include HUS, focal glomerulosclerosis, amyloidosis, glomerulonephritis, diabetes, SLE, and chronic hypoxia/atrophy.

The VEGF variants of the present invention can also be used for treating hypertension. Effectiveness of the treatment is determined by decreased blood pressure particularly in response to salt loading.

The VEGF variants of the present invention can also be useful in treating disorders relating to abnormal transport of solutes across endothelial cells. Such disorders include (1) the treatment or prevention of kidney disease associated with impaired filtration or excretion of solutes; (2) the treatment or prevention of diseases of the central nervous system associated with alterations in cerebrospinal fluid synthesis, composition, or circulation, including stroke, meningitis, tumor, infections, and disorders of bone growth; (3) the treatment or prevention of hypoxia or hypercapnia or fibrosis arising from accumulation of fluid secretions in the lungs or impediments to their removal, including but not restricted to acute respiratory distress syndrome, toxic alveolar injury, as occurs in smoke inhalation, pneumonia, including viral and bacterial infections, surgical intervention, cystic fibrosis, and other inherited or acquired disease of the lung associated with fluid accumulation in the pulmonary air space; (4) the treatment or prevention of pulmonary dysfunction arising from injury to the pulmonary endothelium, including disorders arising from birth prematurity, and primary and secondary causes of pulmonary hypertension; (5) the treatment or prevention of disease arising from disordered transport of fluid and solutes across the intestinal epithelium, including but not restricted to inflammatory bowel disease, infectious diarrhea, and surgical intervention; (6) the treatment or prevention of ascites accumulation in the peritoneum as occurs in failure of the heart, liver, or kidney, or in infectious or tumor states; (7) the enhancement of efficacy of solute flux as it can be needed for peritoneal dialysis in the treatment of kidney failure or installation of therapeutics or nutrition into the peritoneum; (8) the preservation or enhancement of function of organ allografts, including but not restricted to transplants of kidney, heart, liver, lung, pancreas, skin, bone, intestine, and xenografts; and (9) the treatment of cardiac valve disease.

V. Gene Therapy

The present invention also provides delivery vehicles suitable for delivery of a polynucleotide encoding a VEGF variant into cells (whether in vivo, ex vivo, or in vitro). Generally, a polynucleotide encoding a VEGF variant will be operably linked to a promoter and a heterologous polynucleotide. A polynucleotide encoding a VEGF variant can be contained within a cloning or expression vector, using methods well known in the art, or within a viral vector. These vectors (especially expression vectors) can in turn be manipulated to assume any of a number of forms, which may, for example, facilitate delivery to and/or entry into a target cell. Delivery of the polynucleotide constructs of the invention to eukaryotic cells, particularly to mammalian cells, more particularly to distal tubule cells of the kidney, can be accomplished by any suitable art-known method. Delivery can be accomplished in vivo, ex vivo, or in vitro.

The invention provides methods and compositions for transferring such expression constructs into cells, especially in vivo for performing the methods of the present invention. It is also an object of the invention to provide compositions for the treatment (including prevention) of the conditions listed above by providing for the prevention or repair of the underlying vascular injury and/or the associated damage to non-vascular tissues.

Delivery vehicles suitable for incorporation of a polynucleotide encoding a VEGF variant of the present invention for introduction into a host cell include non-viral vehicles and viral vectors. Verma and Somia (1997) *Nature* 389:239–242.

A wide variety of non-viral vehicles for delivery of a polynucleotide encoding a VEGF variant are known in the art and are encompassed in the present invention. A polynucleotide encoding a VEGF variant can be delivered to a cell as naked DNA (U.S. Pat. No. 5,692,622; WO 97/40163). Alternatively, a polynucleotide encoding a VEGF variant can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide encoding a VEGF variant can be associated non-covalently or covalently with these various forms of delivery. Liposomes can be targeted to a particular cell type, e.g., to a glomerular epithelial cell.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldim et al. (1996) *Science* 272:263–267.

Non-viral delivery vehicles comprising a polynucleotide encoding a VEGF variant can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA* 74:3471; and Faller et al. (1984) *J. Virol.* 49:269). For in vivo delivery, the delivery vehicle(s) can be introduced into an individual by any of a number of methods, each of which is familiar in the art.

Further details of the present invention will be apparent from the following non-limiting Examples. All references cited throughout the specification, including the Examples, are hereby expressly incorporated by reference.

EXAMPLES

Example 1

Construction of *Pichia pastoris* Expression Plasmids for the C116S Variant

Figure 15:
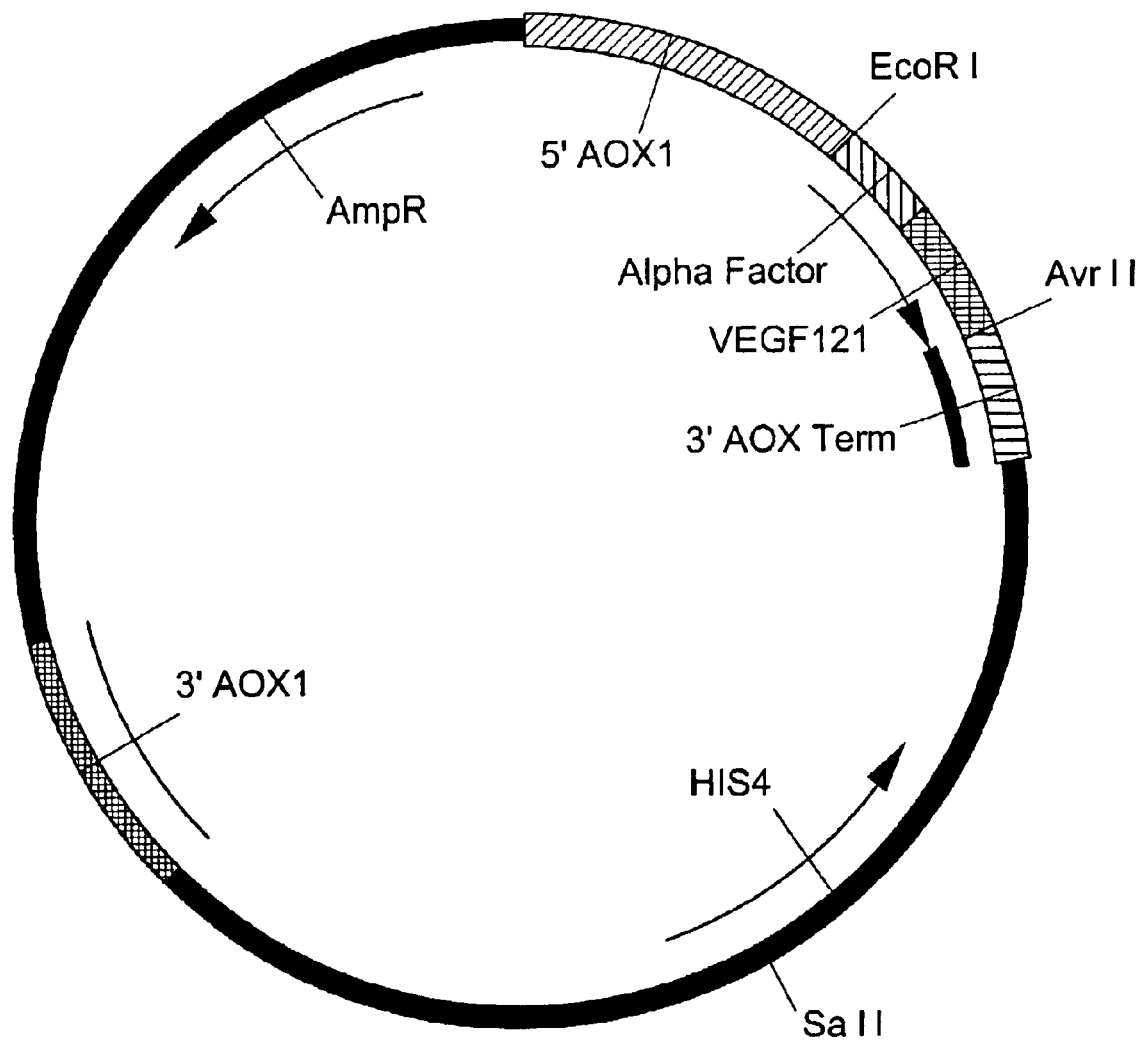
FIG. 15 shows the structure of expression plasmid pAN93.
Figure 16:
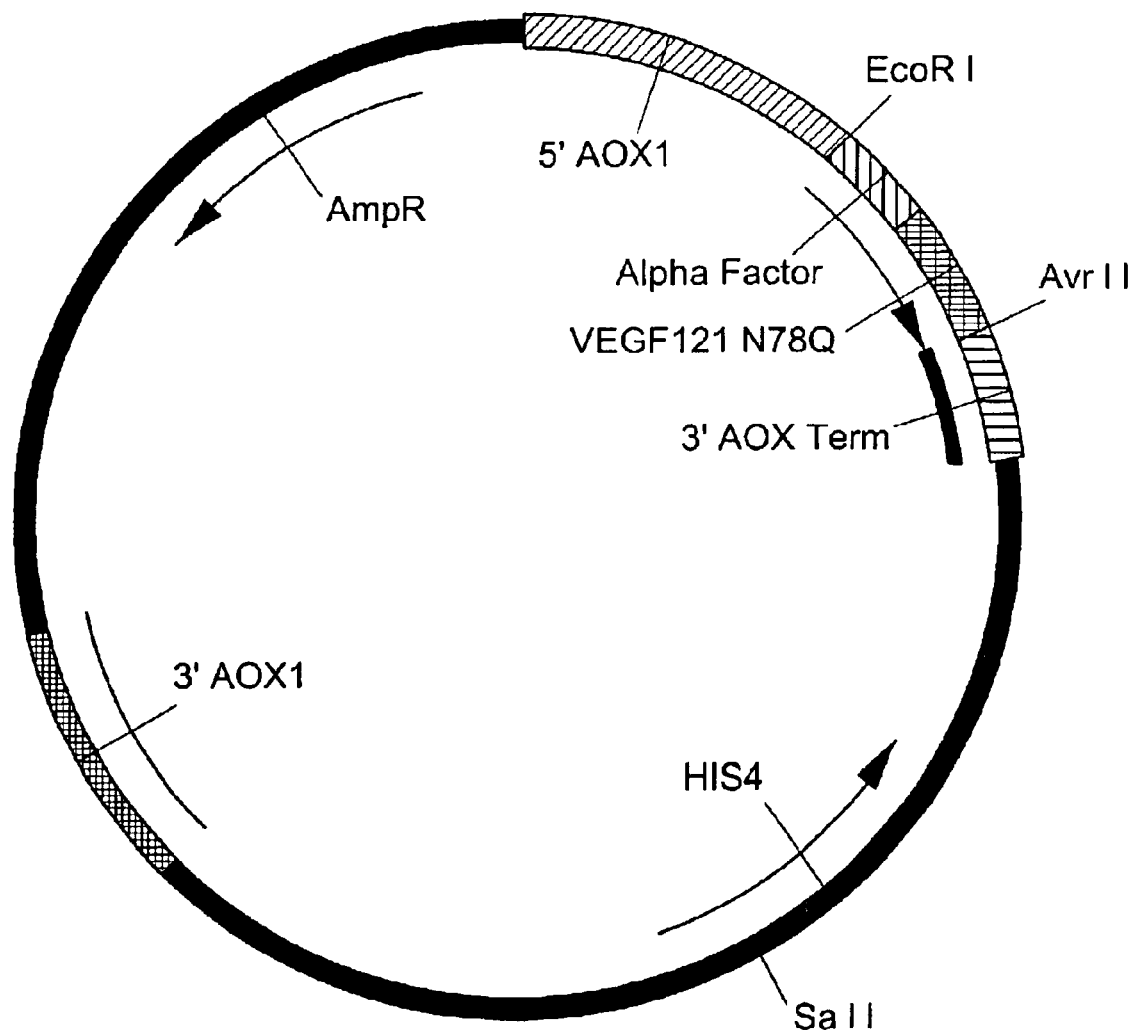
FIG. 16 shows the structure of expression plasmid pAN102.
Figure 17:
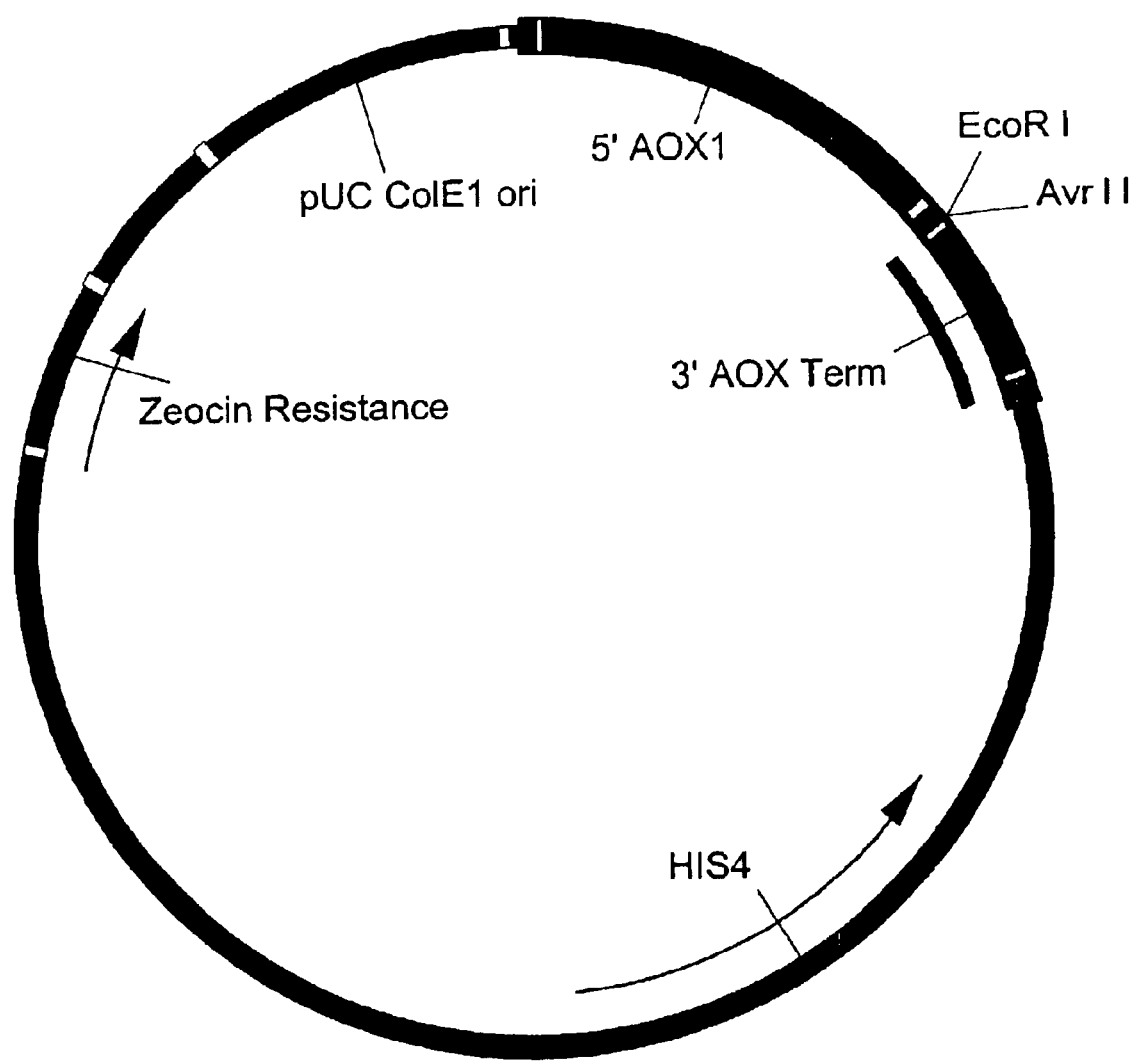
FIG. 17 shows the structure of expression plasmid pAN104.

Since the codon for Cys116 is near the 3' end of the $VEGF_{121}$ gene, the C116S mutation can be introduced by incorporating the mutation (TGT-Cys to TCT-Ser) in a reverse PCR primer that contains the AvrII cloning site. Oligonucleotide primers were constructed with the following sequences:

```
Forward primer Oligo 1612:          (SEQ ID NO:12)
GGGGGGGAATTCGATGAGATTTCCTTCAATTTTTACTGCA Reverse primer Oligo 2524:          (SEQ ID NO:13)
GGGGGGTCCTAGGTCACCGCCTCGGCTTGTCAGATTTTTCTTGTCTTG
``` where the position of the mutation in the reverse primer is underlined. PCR amplification of the $VEGF_{121}$ coding sequences fused at the amino terminus to the alpha factor leader was conducted using as template DNA plasmids pAN93 (wild type $VEGF_{121}$) and pAN102 (N75Q $VEGF_{121}$) (FIGS. 15 and 16). Reaction mixtures consisted of the following m a 50 µl final volume: 1 µl [0.1 µg] of template DNA, 5 µl of a 10 µM solution of each of the primers, 5 µl of a 2 5 mM dideoxynucleotide solution, 1 µl VENT polymerase (New England Biolabs, Beverly, Mass.), and 5 µl reaction buffer supplied by the enzyme manufacturer. The temperature program (94C., 1 min.; 70° C., 1 min.) was repeated for 30 cycles. Five µl of the resulting mixture was examined by electrophoresis and ethidium bromide staining on a 1% agarose gel and a band corresponding to the expected size of 647 bp was observed. The PCR product in each vector was recovered by use of a Spm Gene Clean Kit (Bio201, Vista Calif.) and eluted in a 18 µl final volume. Both PCR fragments as well as the recipient plasmid vector, pAN104 (FIG. 17) were digested with EcoRI and AvrII at 37° C. for 2 hours. DNA was recovered from the reaction using Spin Gene Clean, and purified on a 1% agarose gel and the single visible band was excised from each lane. DNA was purified from the gel slices using Spin Gene Clean. The PCR fragments were each ligated to the pAN104 EcoRI/AvrII vector fragment at 16° C. overnight and 5 μl of each reaction mixture was transformed into *E. coli* TOP10F' cells and plated on selective media containing 50 μg/ml zeocin (Invitrogen, Carlsbad, Calif.). Eight colonies from either the wild type or N75Q mutant transformations were grown up for plasmid DNA preparation. These DNA preparations were digested with EcoRI and AvrII restriction enzymes and the resulting fragment sizes estimated using agarose gel electrophoresis. The expected 647bp band was present in all but two of these digests and two of the correct DNA preparations were chosen for further work. The correct DNA sequence was confirmed using dideoxy chain termination sequencing. These plasmids were named pAN105 (C116S mutant) and pAN106 (N75Q, C116S mutant).

Example 2

Expression of C1116S VEGF121 and N75Q, C116S VEGF121 in *Pichia pastoris*

Plasmids pAN105 and pAN106 were digested with SalI to give linear DNA and transformed by electroporation into *Pichia pastoris* strain GS115. Cells were selected for acquisition of histidine prototrophy by plating on RDB plates and incubating at 30° C. The resulting colonies were also checked for zeocin resistance by streaking on YEPD plates containing 100 μg/ml zeocin. Zeocin resistant transformants were screened for secretion of $VEGF_{121}$ into the media by first inoculating into 2 ml BMGY medium and shaking at 30° C. overnight. Cells were then spun down and resuspended in BMMY medium and incubated in a 30° C. shaker for 48 hours to allow for induction of $VEGF_{121}$, expression. For analysis of $VEGF_{121}$ expression, either 10 or 100 μl of cell supernate was applied to a nitrocellulose membrane by filtration through a 96-well dot blot apparatus. Anti-human VEGF antibody (R&D Systems, Minneapolis, Minn.) was used to detect expression as per manufacturer's specifications. Each of two colonies tested for both pAN105 and pAN106 gave strong positive signals. These new strains were designated ABL191 & ABL192 (pAN105 transformants) and ABL193 and ABL194 (pAN106 transformants). For ABL191 and ABL193, the dot blots were repeated with serial 2-fold dilutions of the conditioned media. Anti-VEGF reactivity was detectable down to an equivalent of 0.025 μl supernatant.

Example 3

Fed-batch Fermentation Process

Materials

The compositions of the media and other materials used in the fed-batch fermentation process are shown in Tables 1–7.

Method

As described in Example 2, N75Q, C116S $VEGF_{121}$ was expressed in *Pichia pastor* is strain GS115 transformed with the expression construct pAN106 (strains ABL193 and ABL194). The host strain is methanol utilization proficient (mut+), capable of growth on methanol as a sole carbon and energy source. The expression construct directs the cell to secrete the VEGF variant into the culture medium in response to the inducer methanol.

Colonies of *P. pastoris* strain GS115 transformed with pAN106 were maintained at 4° C. on YPDS+zeocin plates. A streak plate from a colony was used to generate the inoculum for the fermentation. The inoculum was grown in a baffled, 500-nil shake flask containing 50 ml of YYG medium. The flask was inoculated with a single colony and grown overnight at 30° C. with shaking. The optical density ($OD_{590mm}$) of the resulting culture was 27. This culture was used to inoculate a 10-L fermentor containing 6.0 L of Pichia Fermentation Tank Medium. The temperature of the fermentation was controlled at 30° C. The culture was agitated using an impeller rotation rate of 1000 rpm. The culture was aerated at 16.7 L/min. The pH of the culture was maintained with 2M phosphoric acid and 14.8 M ammonium hydroxide. During the initial batch phase of the fermentation the culture pH was maintained at 4.5. After approximately 17 hours of batch growth, the initial charge of glycerol had been exhausted as evidenced by a rapid rise in the dissolved oxygen (DO) level. The optical density at this time was approximately 60.

The rise in dissolved oxygen level triggered the initiation of the pre-induction phase of the culture, in which the glycerol feed was added at a controlled rate to maintain the DO level at 25% of saturation. The glycerol feed was continued for 4 hours. The induction phase was then initiated.

Initiation of the induction phase entailed terminating the glycerol feed, starting the methanol feed, and adjusting the culture pH. The maximum methanol feed rate was initially 20 ml/min. It was increased to 60 ml/min after 3 hours and increased to 120 ml/min after an additional 1 hour. The maximum methanol feed rate remained at 120 ml/min until harvest. The feed control was programmed to feed at less than the maximal rate if the DO level dropped below 25%. The pH was adjusted (over 1 hour) from 4.5 to 6.0 by addition of 14.8 M ammonium hydroxide. The optical density of the culture, when the methanol feed was initiated, was approximately 120.

Samples were taken from the fermentor every 2 to 4 hours during the day and early evening. Samples were plated to evaluate culture uniformity and viability. The culture pH of samples was measured to gauge whether the in-line pH probe had drifted. The optical density of the samples was measured. As part of sampling during the induction phase, the methanol feed was turned off briefly and the time was measured for the DO to increase by 10%. This DO response time was used to gauge whether methanol was accumulating in the fermentor. Times greater than 2 minutes indicate overfeeding of methanol to a degree which may be toxic to the cells. All response times were 90 seconds or less.

Ninety hours after inoculation the fermentor was harvested. At harvest, the culture temperature was reduced to 25° C. and the culture pH adjusted to 4.0 by addition of 2M phosphoric acid. The final optical density of the culture was 410.

C116S $VEGF_{121}$ was fermented in an analogous fashion.

The fermentation broth was then clarified by centrifugation and the supernatant was filtered. Product in the filtered supernatant was then continuously processed by cation exchange chromatography (SP-Streamline, Pharmacia). The material captured was further purified by reverse-phase HPLC (C4, YMC). The fraction were collected, and concentration of the VEGF variant was determined. For further details of purification see, e.g. Muller et al, *Proc. Natl. Acad. Sci. USA* 94:7192–7197 (1997).

TABLE 1

YYG Medium

| Ingredient | Amount |
| --- | --- |
| Yeast Extract | 10.0 g |
| Yeast Nitrogen Base | 13.4 g |
| Biotin | 0.4 mg |
| Glycerol | 20 mL |
| 1M Potassium Phosphate Buffer (see below) | 250 mL |
| $H_2O$ | Up to 1 L | pH is approximately 6.0 without adjustment
Sterilize with autoclave

TABLE 2

1M Potassium Phosphate Buffer

| | |
| --- | --- |
| $KH_2PO_4$ | 118 g |
| $K_2HPO_4$ | 23 0 g |
| $H_2O$ | Up to 1 L |

Adjust pH to 6.0 with NaOH
Sterilize by filtration

TABLE 3

YPDS + Zeocin Plates

| Ingredient | Amount |
| --- | --- |
| Yeast Extract | 10.0 g |
| Sorbitol | 182.2 g |
| Peptone | 20 0 g |
| Agar | 20 0 g |
| $H_2O$ | 900 mL |
| Glucose* | 40 g |
| 100 mg/ml Zeocin** | 1.0 mL |

*Sterilized separately with autoclave
**Sterilized separately by filtration

TABLE 4

PTM1 Trace Minerals with Biotin

| Ingredient | Amount |
| --- | --- |
| $CuSO_4 5H_2O$ | 6.00 g |
| NaI | 0.08 g |
| $MnSO_4 H_2O$ | 3.00 g |
| $Na_2MoO_4 2H_2O$ | 0.20 g |
| $H_3BO_3$ | 0.02 g |
| $CoCl_2 6H_2O$ | 0.91 g |
| $ZnCl_2$ | 20.00 g |
| $FeCl_3 6H_2O$ | 20.78 g |
| $H_2SO_4$ | 5.00 mL |
| Biotin | 0.2 g |
| $H_2O$ | Up to 1.00 L |

TABLE 5

Pichia Fermentation Tank Medium

| Ingredient | Amount |
| --- | --- |
| 85% $H_3PO_4$ | 8.4 mL |
| $CaCl_2 2H_2O$ | 1.08 g |
| $K_2SO_4$ | 8.60 g |
| $MgSO_4$ | 7.02 g |
| KOH | 1.95 g |
| Peptone | 10.0 g |

TABLE 5-continued

Pichia Fermentation Tank Medium

| Ingredient | Amount |
| --- | --- |
| Adjust pH to 4.5 (with NaOH) then add | |
| Glycerol | 22.5 g |
| Sterilize in fermentor then add | |
| PTM1 Trace Minerals with Biotin (see below) | 4.0 mL |
| 0.20 g/L Biotin | 8.0 mL |

TABLE 6

Glycerol Feed

| Ingredient | Amount |
| --- | --- |
| Glycerol | 500 mL |
| Water | Up to 1000 mL |
| Sterilize in autoclave and then add | |
| PTM1 Trace Minerals with Biotin | 12.0 mL |

TABLE 7

Methanol Feed

| Ingredient | Amount |
| --- | --- |
| Methanol | 1 L |
| Filter sterilize and then add | |
| PTM1 Trace Minerals with Biotin | 12.0 mL |

Example 4

HUVE Cell Proliferation Assay—BrdU ELISA Assay 96-well plates were coated with human fibronectin (Sigma;1 μg/100 μl/well) in phosphate-buffered saline (PBS). The plates were incubated at room temperature for 45 minutes, the fibronectin solution was aspirated, and the plates were dried for 20–30 minutes open to air. Cells (HUVEC, Clonetics) were then plated at 10000 cells/100 μl/well in serum free medium) human endothelial cell serum free medium; (Gibco)+2% fetal bovine serum (FBS), leaving the first column cell-free to act as a blank. The cells were incubated at 37° C., 5% $CO_2$ overnight (18–24 hours). The medium was changed to 100 μl/well serum free medium+1% FBS, and the plates were incubated at 37° C., 5% $CO_2$ for 24 hours to allow the cells to quiesce.

$VEGF_{121}$ standards and the samples to be tested were diluted serially 1:3 in serum-free medium 0.1% human serum albumin (HSA, Sigma). 10 μl of the dilutions were added to the wells, which were incubated at 37° C., 5% $CO_2$ for 24 hours. BrdU solution from the Cell Proliferation USA kit (Boehringer Mannheim) was diluted 1:100 with Gibco serum-free medium, and 12 μl of this solution was added to each well. The plates were then incubated at 37° C., 5% $CO_2$ for 4–5 hours. BrdU was omitted for the wells used as background control.

After the 4–5 hours incubation, the medium was aspirated, 200 μl FixDeNat solution was added to each well, and the plates were incubated at room temperature for 30 minutes. FixDeNat was thoroughly aspirated, 100 μl anti-BrdU-POD (anti-BrdU-peroxidase) antibody solution was added to each well (1: 100 dilution of anti-BrdU-POD into PBS+0.05% Tween20+0.5% HSA), and the plates were incubated at room temperature for 90 minutes. Wells were washed three times with 300 µl/well of PBS+0.05% Tween20, and 100 µl TMB substrate was added. This was followed by incubation for 20–30 minutes until the color was sufficient for colorimetric reading, whereupon 50 µl sulfuric acid (5N) was added, and colorimetric reading was performed at an absorbance of 450 nm.

Results

Figure 13:
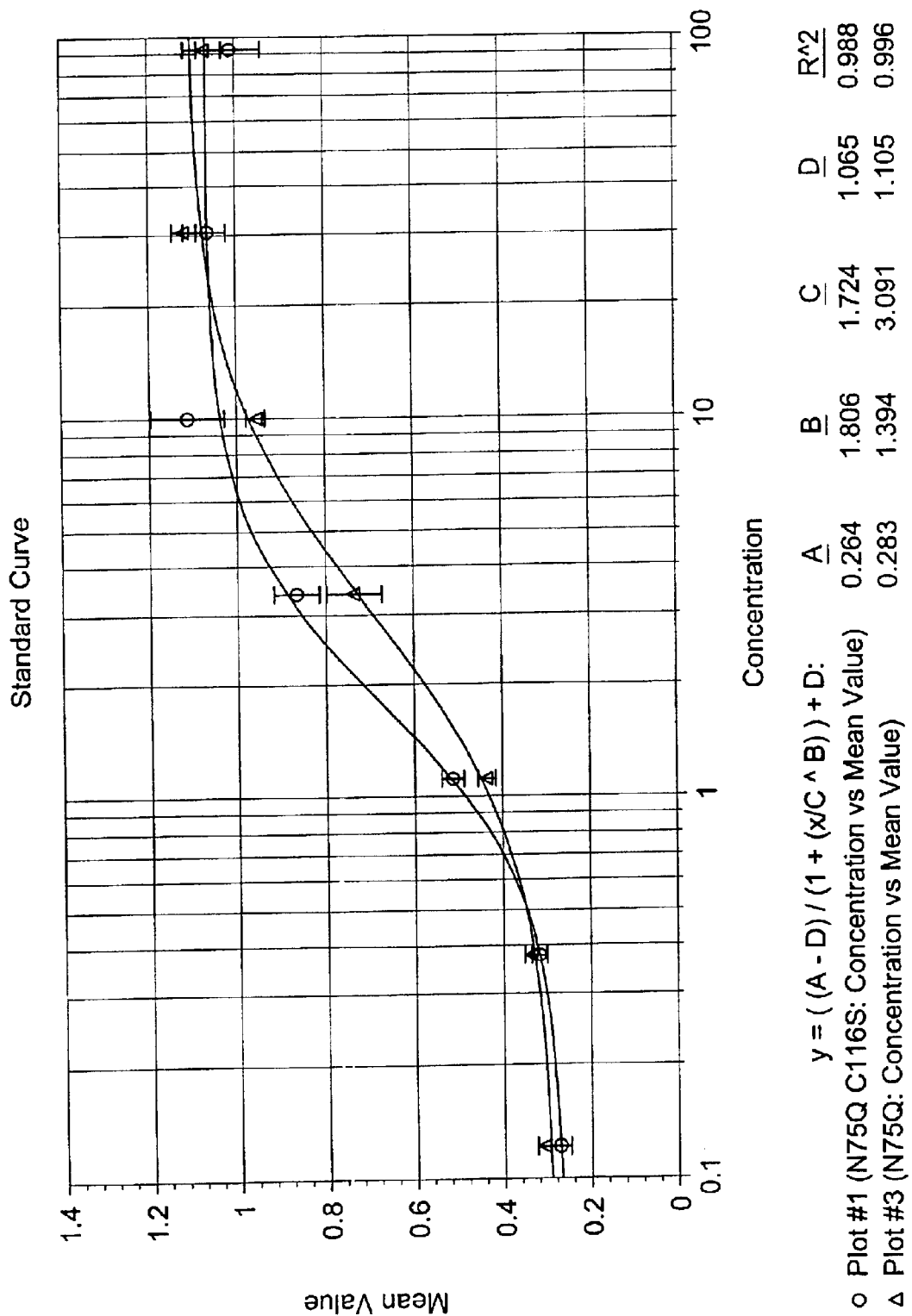
FIGS. 13 and 14 show the results from two separate tests in the HUVEC proliferation assay. The graphs depict the amount of DNA synthesis that was stimulated in response to serial dilutions of Pichia-derived N75QVEGF$_{121}$ vs. N75QC116SVEGF$_{121}$. The X axis of each graph represents the final concentration of added growth factor in the assay wells, expressed as ng/ml. The y axis represents the optical density recorded in each well after use of the BrdU kit (Boehringer Mannheim) to detect incorporated bromodeoxyuridine at the end of the assay.
Figure 14:
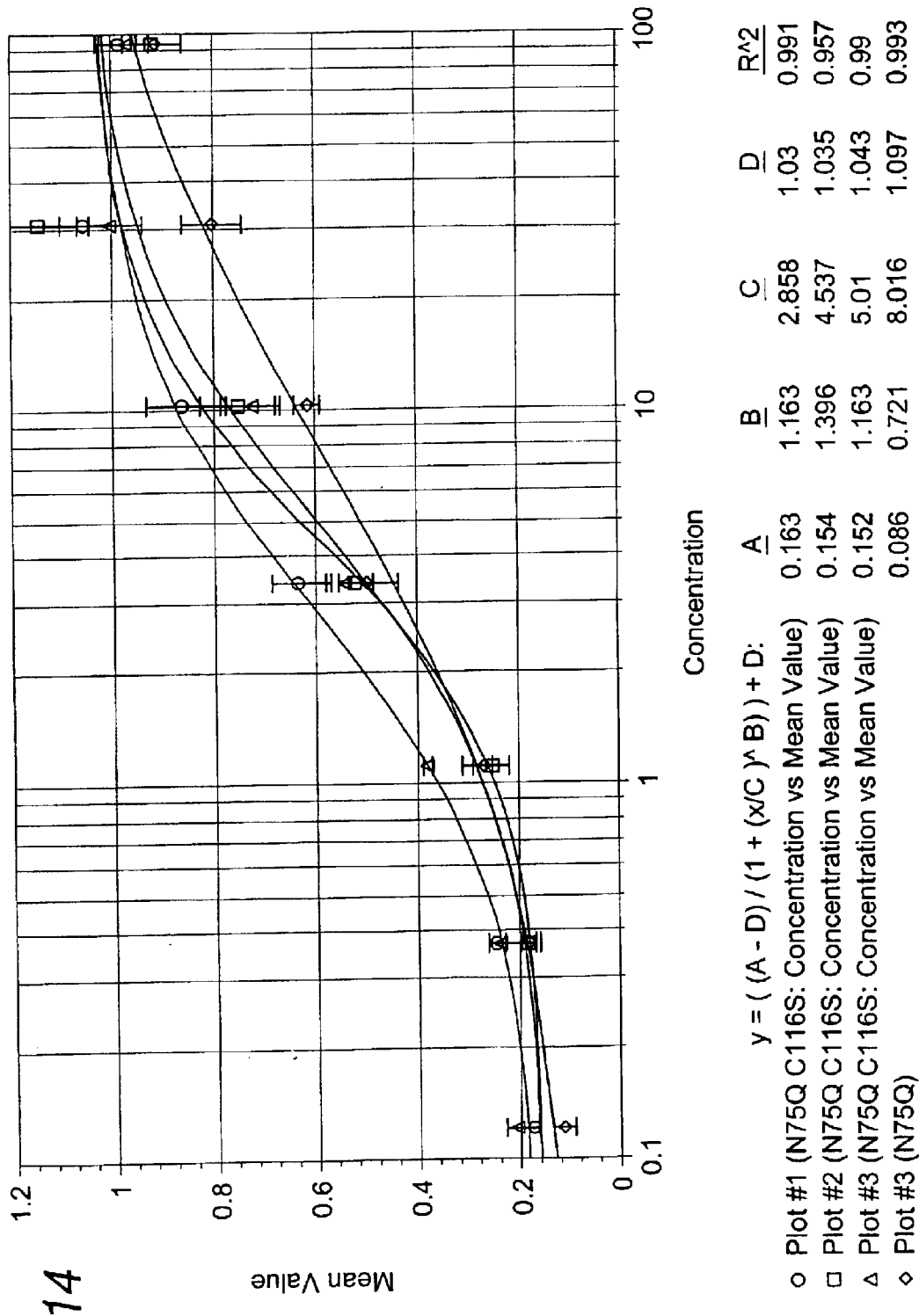

The results are shown in FIGS. 13 and 14. The graphs depict the amount of DNA synthesis that was stimulated in response to serial dilutions of Pichia-derived N75Q VEGF$_{121}$ vs. N75Q,C116S VEGF$_{121}$. The X axis of each graph represents the final concentration of added growth factor in the assay wells, expressed as ng/ml. The y axis represents the optical density recorded in each well after use of the BrdU kit (Boehringer Mannheim) to detect incorporated bromodeoxyuridine at the end of the assay.

In the case of the experiment shown in FIG. 13, the ED$_{50}$ (effective dose of growth factor needed to achieve a half-maximal proliferation response) for N17Q, C116S $VEGF_{121}$ was 1.72 ng/ml, while N75Q $VEGF_{121}$ showed an $ED_{50}$ of 3.09 ng/ml. In the experiment shown in FIG. 14, the $ED_{50}$'s for N75Q, C116S $VEGF_{121}$ and N75Q $VEGF_{121}$ were 2.86 and 8.02 ng/ml, respectively. Thus, in each case, the N75Q, C116S $VEGF_{121}$ variant was significantly more potent than N75Q $VEGF_{121}$ in promoting DNA synthesis (by 1.7 to 2.8-fold).

What is claimed is:

1. A method of inducing angiogenesis comprising:

administering an effective amount of a vascular endothelial growth factor VEGF ($hVEGF_{121}$) variant to a patient in need thereof, wherein the VEGF variant comprises amino acids 27–147 of SEQ ID NO:2, and wherein SEQ ID NO:2 has been altered by an amino acid substitution or deletion at (position 142 of SEQ ID NO:2); and wherein SEQ ID NO:2 has been altered by an amino acid substitution or deletion at position 101, 102, or 103, such that the variant is not glycosylated, said variant having at least 85% sequence identity with hVEGF121 polypeptide (amino acids 27–147 of SEQ ID NO:2), whereby angiogenesis is induced by the VEGF variant administered.

2. The method of claim 1, wherein angiogenesis is induced to prevent or repair injury to blood vessels.

3. The method of claim 2, wherein said injury is associated with microvascular angiopathy.

4. The method of claim 3, wherein said microvascular angiopathy is thrombotic microangiopathy (TMA).

5. The method of claim 2, wherein said injury is associated with hemolytic-uremic syndrome (HUS).

6. The method of claim 1, wherein the cysteine (C) residue is substituted by a different amino acid residue.

7. The method of claim 6, wherein the different amino acid residue is a serine (S) residue.

8. The method of claim 6, wherein, apart from the substitution at position 142 and the removal of the glycosylation site at position 101–103, the VEGF variant retains the amino acid sequence of $hVEGF_{121}$ (amino acids 27–147 of SEQ ID NO:2).

9. The method of claim 1, wherein removing the N-linked glycosylation site from the encoding nucleic acid sequence to produce a VEGF variant comprises removing the N-linked glycosylation site using site-directed mutagenesis.

10. The method of claim 9, wherein removing the N-linked glycosylation site from the encoding nucleic acid sequence to produce a VEGF variant comprises substituting at least one residue in the asparagine-isoleucine-threonine (N-I-T) glycosylation site at position 101–103 of $hVEGF_{121}$.

11. The method of claim 10, wherein asparagine (N) at position 101 is substituted by another amino acid.

12. The method of claim 11, wherein the another amino acid is glutamine (Q).

13. The method of claim 1, wherein the VEGF variant is C142S of SEQ ID NO: 2 $hVEGF_{121}$.

14. The method of claim 1, wherein the VEGF variant additionally comprises an N-terminal substitution of SEQ ID NO: 2.

15. The method of claim 14, wherein said substitution is within the first 10 amino acids of $hVEGF_{121}$.

16. The method of claim 15, wherein said substitution is at amino acid position 5 of $hVEGF_{121}$.

17. The method of claim 16, wherein said substitution is X5D, wherein X is an amino acid at position 5 of $hVEGF_{121}$.

* * * * *

SEQUENCE LISTING

```
<160> NUMBER OF SEQ ID NOS: 11
<210> SEQ ID NO 1
<211> LENGTH: 444
<212> TYPE: DNA
<213> ORGANISM: HOMO SAPIEN
<220> FEATURE:
<221> NAME/KEY: CDS
<222> LOCATION: (1)...(441)

<400> SEQUENCE: 1 atg aac ttt ctg ctg tct tgg gtg cat tgg agc ctt gcc ttg ctg ctc       48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga       96
Tyr Leu His His Ala Lys Trp Ser Gln Ala Ala Pro Met Ala Glu Gly
            20                  25                  30 gga ggg cag aat cat cac gaa gtg gtg aag ttc atg gat gtc tat cag      144
Gly Gly Gln Asn His His Glu Val Val Lys Phe Met Asp Val Tyr Gln
        35                  40                  45 cgc agc tac tgc cat cca atc gag acc ctg gtg gac atc ttc cag gag      192
Arg Ser Tyr Cys His Pro Ile Glu Thr Leu Val Asp Ile Phe Gln Glu
    50                  55                  60 tac cct gat gag atc gag tac atc ttc aag cca tcc tgt gtg ccc ctg      240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc      288
Met Arg Cys Gly Gly Cys Cys Asn Asp Glu Gly Leu Glu Cys Val Pro
                85                  90                  95 act gag gag tcc aac atc acc atg cag att atg cgg atc aaa cct cac      336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt      384
Gln Gly Gln His Ile Gly Glu Met Ser Phe Leu Gln His Asn Lys Cys
        115                 120                 125 gaa tgc aga cca aag aaa gat aga gca aga caa gaa aaa tgt gac aag      432
Glu Cys Arg Pro Lys Lys Asp Arg Ala Arg Gln Glu Lys Cys Asp Lys
    130                 135                 140 ccg agg cgg tga                                                      444
Pro Arg Arg
145

<210> SEQ ID NO 2
<211> LENGTH: 147
<212> TYPE: PRT
<213> ORGANISM: Homo sapiens
```

```
<400> SEQUENCE: 2

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
         50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Cys Asp Lys
        130                 135                 140

Pro Arg Arg
145

<210> SEQ ID NO 3
<211> LENGTH: 516
<212> TYPE: DNA
<213> ORGANISM: Homo sapiens
<220> FEATURE:
<221> NAME/KEY: CDS
<222> LOCATION: (1)...(513)

<400> SEQUENCE: 3 atg aac ttt ctg ctg tct tgg gtg gat tgg agc ctt gcc ttg ctg ctc    48
Met Asn Phe Leu Leu Ser Trp Val Asp Trp Ser Leu Ala Leu Leu Leu
  1               5                  10                  15 tac ctc cac cat gcc aag tgg tcc cag gct gca ccc atg gca gaa gga    96
Tyr Leu His His Ala Lys Trp Ser Gln Ala Ala Pro Met Ala Glu Gly
                 20                  25                  30 gga ggg cag aat cat cac gaa gtg gtg aag ttc atg gat gtc tat cag   144
Gly Gly Gln Asn His His Glu Val Val Lys Phe Met Asp Val Tyr Gln
             35                  40                  45 cgc agc tac tgc cat cca atc gag acc ctg gtg gac atc ttc cag gag   192
Arg Ser Tyr Cys His Pro Ile Glu Thr Leu Val Asp Ile Phe Gln Glu
         50                  55                  60 tac cct gat gag atc gag tac atc ttc aag cca tcc tgt gtg ccc ctg   240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc   288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac   336
Thr Glu Glu Ser Asn Ile Thr Met Gln Ile Met Arg Ile Lys Pro His
                100                 105                 110 caa ggc cag cac ata gga gag atg agc ttc cta cag cac aac aaa tgt   384
Gln Gly Gln His Ile Gly Glu Met Ser Phe Leu Gln His Asn Lys Cys
            115                 120                 125 gaa tgc aga cca aag aaa gat aga gca aga caa gaa aaa aaa tca gtt   432
Glu Cys Arg Pro Lys Lys Asp Arg Ala Arg Gln Glu Lys Lys Ser Val
        130                 135                 140
```

```
cga gga aag gga aag ggg caa aaa cga aag cgc aag aaa tcc cgg tat    480
Arg Gly Lys Gly Lys Gly Gln Lys Arg Lys Arg Lys Lys Ser Arg Tyr
145                 150                 155                 160 aag tcc tgg agc gta tgt gac aag ccg agg cgg tga                    516
Lys Ser Trp Ser Val Cys Asp Lys Pro Arg Arg
                165                 170
```

<210> SEQ ID NO 4
<211> LENGTH: 145
<212> TYPE: PRT
<213> ORGANISM: Homo sapiens

<400> SEQUENCE: 4

```
Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Cys Asp Lys Pro Arg
    130                 135                 140

Arg
145
```

<210> SEQ ID NO 5
<211> LENGTH: 576
<212> TYPE: DNA
<213> ORGANISM: Homo sapiens
<220> FEATURE:
<221> NAME/KEY: CDS
<222> LOCATION: (1)...(573)

<400> SEQUENCE: 5

```
atg aac ttt ctg ctg tct tgg gtg cat tgg agc ctc gcc ttg ctg ctc    48
Met Asn Phe Leu Leu Ser Trp Val His Trp Ser Leu Ala Leu Leu Leu
1               5                   10                  15 tac ctc cac cat gcc aag tgg tcc cag gct gca ccc atg gca gaa gga    96
Tyr Leu His His Ala Lys Trp Ser Gln Ala Ala Pro Met Ala Glu Gly
            20                  25                  30 gga ggg cag aat cat cac gaa gtg gtg aag ttc atg gat gtc tat cag    144
Gly Gly Gln Asn His His Glu Val Val Lys Phe Met Asp Val Tyr Gln
        35                  40                  45 cgc agc tac tgc cat cca atc gag acc ctg gtg gac atc ttc cag gag    192
Arg Ser Tyr Cys His Pro Ile Glu Thr Leu Val Asp Ile Phe Gln Glu
    50                  55                  60 tac cct gat gag atc gag tac atc ttc aag cca tcc tgt gtg ccc ctg    240
Tyr Pro Asp Glu Ile Glu Tyr Ile Phe Lys Pro Ser Cys Val Pro Leu
65                  70                  75                  80 atg cga tgc ggg ggc tgc tgc aat gac gag ggc ctg gag tgt gtg ccc    288
Met Arg Cys Gly Gly Cys Cys Asn Asp Glu Gly Leu Glu Cys Val Pro
```

```
act gag gag tcc aac atc acc atg cag att atg cgg atc aaa cct cac      336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt      384
Gln Gly Gln His Ile Gly Glu Met Ser Phe Leu Gln His Asn Lys Cys
            115                 120                 125 gaa tgc aga cca aag aaa gat aga gca aga caa gaa aat ccc tgt ggg      432
Glu Cys Arg Pro Lys Lys Asp Arg Ala Arg Gln Glu Asn Pro Cys Gly
    130                 135                 140 cct tgc tca gag cgg aga aag cat ttg ttt gta caa gat ccg cag acg      480
Pro Cys Ser Glu Arg Arg Lys His Leu Phe Val Gln Asp Pro Gln Thr
145                 150                 155                 160 tgt aaa tgt tcc tgc aaa aac aca gac tcg cgt tgc aag gcg agg cag      528
Cys Lys Cys Ser Cys Lys Asn Thr Asp Ser Arg Cys Lys Ala Arg Gln
                165                 170                 175 ctt gag tta aac gaa cgt act tgc aga tgt gac aag ccg agg cgg          573
Leu Glu Leu Asn Glu Arg Thr Cys Arg Cys Asp Lys Pro Arg Arg
                180                 185                 190 tga                                                                  576
```

<210> SEQ ID NO 6
<211> LENGTH: 191
<212> TYPE: PRT
<213> ORGANISM: Homo sapiens

<400> SEQUENCE: 6

```
Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
     50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 7
<211> LENGTH: 642
<212> TYPE: DNA
<213> ORGANISM: Homo sapiens
<220> FEATURE:
<221> NAME/KEY: CDS

```
<222> LOCATION: (1)...(639)

<400> SEQUENCE: 7 atg aac ttt ctg ctg tct tgg gtg cat tgg agc ctc gcc ttg ctg ctc        48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga        96
Tyr Leu His His Ala Lys Trp Ser Gln Ala Ala Pro Met Ala Glu Gly
             20                  25                  30 gga ggg cag aat cat cac gaa gtg gtg aag ttc atg gat gtc tat cag       144
Gly Gly Gln Asn His His Glu Val Val Lys Phe Met Asp Val Tyr Gln
         35                  40                  45 cgc agc tac tgc cat cca atc gag acc ctg gtg gac atc ttc cag gag       192
Arg Ser Tyr Cys His Pro Ile Glu Thr Leu Val Asp Ile Phe Gln Glu
 50                  55                  60 tac cct gat gag atc gag tac atc ttc aag cca tcc tgt gtg ccc ctg       240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc       288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac       336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt       384
Gln Gly Gln His Ile Gly Glu Met Ser Phe Leu Gln His Asn Lys Cys
        115                 120                 125 gaa tgc aga cca aag aaa gat aga gca aga caa gaa aaa aaa tca gtt       432
Glu Cys Arg Pro Lys Lys Asp Arg Ala Arg Gln Glu Lys Lys Ser Val
130                 135                 140 cga gga aag gga aag ggg caa aaa cga aag cgc aag aaa tcc cgg tat       480
Arg Gly Lys Gly Lys Gly Gln Lys Arg Lys Arg Lys Lys Ser Arg Tyr
145                 150                 155                 160 aag tcc tgg agc gtg ggg cct tgc tca gag cgg aga aag cat ttg ttt       528
Lys Ser Trp Ser Val Gly Pro Cys Ser Glu Arg Arg Lys His Leu Phe
                165                 170                 175 gta caa gat ccg cag acg tgt aaa tgt tcc tgc aaa aac aca gac tcg       576
Val Gln Asp Pro Gln Thr Cys Lys Cys Ser Cys Lys Asn Thr Asp Ser
            180                 185                 190 cgt tgc aag gcg agg cag ctt gag tta aac gaa cgt act tgc aga tgt       624
Arg Cys Lys Ala Arg Gln Leu Glu Leu Asn Glu Arg Thr Cys Arg Cys
        195                 200                 205 gac aag ccg agg cgg tga                                               642
Asp Lys Pro Arg Arg
    210

<210> SEQ ID NO 8
<211> LENGTH: 213
<212> TYPE: PRT
<213> ORGANISM: Homo sapiens

<400> SEQUENCE: 8

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
 50                  55                  60
```

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Gly Pro Cys Ser Glu Arg Arg Lys His Leu Phe
                165                 170                 175

Val Gln Asp Pro Gln Thr Cys Lys Cys Ser Cys Lys Asn Thr Asp Ser
            180                 185                 190

Arg Cys Lys Ala Arg Gln Leu Glu Leu Asn Glu Arg Thr Cys Arg Cys
            195                 200                 205

Asp Lys Pro Arg Arg
        210

<210> SEQ ID NO 9
<211> LENGTH: 699
<212> TYPE: DNA
<213> ORGANISM: Homo sapiens
<220> FEATURE:
<221> NAME/KEY: CDS
<222> LOCATION: (1)...(696)

<400> SEQUENCE: 9 atg aac ttt ctg ctg tct tgg gtg cat tgg agc ctc gcc ttg ctg ctc      48
Met Asn Phe Leu Leu Ser Trp Val His Trp Ser Leu Ala Leu Leu Leu
1               5                   10                  15 tac ctc cac cat gcc aag tgg tcc cag gct gca ccc atg gca gaa gga      96
Tyr Leu His His Ala Lys Trp Ser Gln Ala Ala Pro Met Ala Glu Gly
                20                  25                  30 gga ggg cag aat cat cac gaa gtg gtg aag ttc atg gat gtc tat cag     144
Gly Gly Gln Asn His His Glu Val Val Lys Phe Met Asp Val Tyr Gln
            35                  40                  45 cgc agc tac tgc cat cca atc gag acc ctg gtg gac atc ttc cag gag     192
Arg Ser Tyr Cys His Pro Ile Glu Thr Leu Val Asp Ile Phe Gln Glu
50                  55                  60 tac cct gat gag atc gag tac atc ttc aag cca tcc tgt gtg ccc ctg     240
Tyr Pro Asp Glu Ile Glu Tyr Ile Phe Lys Pro Ser Cys Val Pro Leu
65                  70                  75                  80 atg cga tgc ggg ggc tgc tgc aat gac gag ggc ctg gag tgt gtg ccc     288
Met Arg Cys Gly Gly Cys Cys Asn Asp Glu Gly Leu Glu Cys Val Pro
                85                  90                  95 act gag gag tcc aac atc acc atg cag att atg cgg atc aaa cct cac     336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt     384
Gln Gly Gln His Ile Gly Glu Met Ser Phe Leu Gln His Asn Lys Cys
            115                 120                 125 gaa tgc aga cca aag aaa gat aga gca aga caa gaa aaa aaa tca gtt     432
Glu Cys Arg Pro Lys Lys Asp Arg Ala Arg Gln Glu Lys Lys Ser Val
130                 135                 140 cga gga aag gga aag ggg caa aaa cga aag cgc aag aaa tcc cgg tat     480

```
Arg Gly Lys Gly Lys Gly Gln Lys Arg Lys Arg Lys Lys Ser Arg Tyr
145                 150                 155                 160 aag tcc tgg agc gtg tac gtt ggt gcc cgc tgc tgt cta atg ccc tgg    528
Lys Ser Trp Ser Val Tyr Val Gly Ala Arg Cys Cys Leu Met Pro Trp
                165                 170                 175 agc ctc cct ggc ccc cat ccc tgt ggg cct tgc tca gag cgg aga aag    576
Ser Leu Pro Gly Pro His Pro Cys Gly Pro Cys Ser Glu Arg Arg Lys
            180                 185                 190 cat ttg ttt gta caa gat ccg cag acg tgt aaa tgt tcc tgc aaa aac    624
His Leu Phe Val Gln Asp Pro Gln Thr Cys Lys Cys Ser Cys Lys Asn
        195                 200                 205 aca gac tcg cgt tgc aag gcg agg cag ctt gag tta aac gaa cgt act    672
Thr Asp Ser Arg Cys Lys Ala Arg Gln Leu Glu Leu Asn Glu Arg Thr
    210                 215                 220 tgc aga tgt gac aag ccg agg cgg tga                                699
Cys Arg Cys Asp Lys Pro Arg Arg
225                 230

<210> SEQ ID NO 10
<211> LENGTH: 232
<212> TYPE: PRT
<213> ORGANISM: Homo sapiens

<400> SEQUENCE: 10

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 11
<211> LENGTH: 110
```

-continued

```
<212> TYPE: PRT
<213> ORGANISM: Homo sapiens

<400> SEQUENCE: 11

Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
            100                 105                 110
```